(12) United States Patent
Zong et al.

(10) Patent No.: US 10,563,042 B2
(45) Date of Patent: Feb. 18, 2020

(54) QUATERNARY CATIONIC POLYMERS

(71) Applicant: ECOLAB USA, INC., St. Paul, MN (US)

(72) Inventors: Zhengang Zong, Aurora, IL (US); Kun Xiong, Naperville, IL (US); Jeffrey R. Cramm, Batavia, IL (US); Xiaodong Huang, Aurora, IL (US); Jeremy Moloney, Katy, TX (US); Ashish Dhawan, Naperville, IL (US)

(73) Assignee: ECOLAB USA INC., St. Paul, MN (US)

( * ) Notice: Subject to any disclaimer, the term of this patent is extended or adjusted under 35 U.S.C. 154(b) by 139 days.

(21) Appl. No.: 15/839,502

(22) Filed: Dec. 12, 2017

(65) Prior Publication Data

US 2018/0163020 A1     Jun. 14, 2018

Related U.S. Application Data

(60) Provisional application No. 62/433,967, filed on Dec. 14, 2016, provisional application No. 62/433,903, filed on Dec. 14, 2016.

(51) Int. Cl.
| | | |
|---|---|---|
| *C08K 5/19* | (2006.01) | |
| *C08L 79/02* | (2006.01) | |
| *C08L 79/08* | (2006.01) | |
| *C08J 7/12* | (2006.01) | |
| *A01N 25/10* | (2006.01) | |

(52) U.S. Cl.
CPC ........... *C08K 5/19* (2013.01); *C08J 7/12* (2013.01); *C08L 79/02* (2013.01); *C08L 79/08* (2013.01); *A01N 25/10* (2013.01)

(58) Field of Classification Search
CPC .. C08K 5/19; C08L 79/02; C08L 79/08; C08J 7/12; A01N 25/10
See application file for complete search history.

(56) References Cited

U.S. PATENT DOCUMENTS

| | | | |
|---|---|---|---|
| 3,152,188 A | 10/1964 | Kirkpatrick et al. | |
| 3,678,098 A * | 7/1972 | Lewis | C07D 303/36 526/292.2 |
| 3,718,639 A | 2/1973 | Falkehag et al. | |
| 4,054,542 A | 10/1977 | Buckman et al. | |
| 4,155,855 A * | 5/1979 | Goffinet | C11D 1/62 510/516 |
| 4,166,073 A | 8/1979 | Bauman | |
| 4,381,259 A | 4/1983 | Homma et al. | |
| 4,390,689 A | 6/1983 | Jaquet et al. | |
| 4,506,081 A * | 3/1985 | Fenyes | A01N 33/12 548/523 |
| 4,605,707 A | 8/1986 | Rheimschussel et al. | |
| 4,978,685 A | 12/1990 | Gannon et al. | |
| 4,995,944 A | 2/1991 | Aston et al. | |
| 5,171,350 A | 12/1992 | Stainer | |
| 5,643,498 A | 7/1997 | Li et al. | |
| 5,716,917 A | 2/1998 | Williams et al. | |
| 5,735,941 A | 4/1998 | Feeman et al. | |
| 5,783,092 A | 7/1998 | Brown et al. | |
| 5,912,306 A | 6/1999 | Pudney et al. | |
| 6,153,568 A | 11/2000 | McCanna et al. | |
| 6,238,521 B1 | 5/2001 | Shing et al. | |
| 6,436,237 B1 | 8/2002 | Berckmans et al. | |
| 6,472,360 B1 | 10/2002 | Beggs et al. | |
| 6,656,977 B2 | 12/2003 | Slone et al. | |
| 6,784,168 B1 | 8/2004 | Jones et al. | |
| 6,969,443 B1 | 11/2005 | Kokko | |
| 7,399,821 B2 | 7/2008 | Mandeville, III et al. | |
| 7,431,799 B2 | 10/2008 | Antal et al. | |
| 7,939,485 B2 | 5/2011 | Price et al. | |
| 7,947,854 B2 | 5/2011 | Widmer et al. | |
| 7,951,754 B2 | 5/2011 | Tiwari et al. | |
| 8,012,461 B2 | 9/2011 | Whitely et al. | |
| 8,163,075 B2 | 4/2012 | Kennedy et al. | |
| 8,512,722 B2 | 8/2013 | Lee et al. | |
| 9,216,944 B2 | 12/2015 | Moonen et al. | |
| 9,247,736 B2 | 2/2016 | Ylitalo et al. | |
| 9,642,369 B2 | 5/2017 | Porosa et al. | |
| 2004/0180970 A1 | 9/2004 | Kretz et al. | |

(Continued)

FOREIGN PATENT DOCUMENTS

| | | |
|---|---|---|
| CN | 101486657 A | 7/2009 |
| CN | 101560380 A | 10/2009 |

(Continued)

OTHER PUBLICATIONS

Angeloni, Annino Santa et al., The Mannich bases in polymer synthesis: 3. Reduction of poly(β-aminoketone)s to poly(γ-aminoalcohols)s and their N-alkylation to poly(γ-hydroxy quaternary ammonium salt)s, Polymer (Oct. 1982) 23(11): 1693-1697.

Ayfer, Burcu et al., "Synthesis and antibacterial activities of new quaternary ammonium monomers," Designed Monomers and Polymers (2005) 8(5): 437-451.

Badawy, Mohamed E.I. et al., "Antimicrobial and inhibitory enzyme activity of N-(benzyl) and quaternary N-(benzyl) chitosan derivatives on plant pathogens," Carbohydrate Polymers (Oct. 2014) 111: 670-682.

Duan, Ming et al., "Treatment of wastewater produced from polymer flooding using polyoxyalkylated polyethyleneimine," Separation and Purification Technology (Sep. 8, 2014) 133: 160-167.

(Continued)

*Primary Examiner* — Robert D Harlan
(74) *Attorney, Agent, or Firm* — Eric D. Babych; Barnes & Thornburg LLP

(57) ABSTRACT

A cationic polymer salt composition is provided that includes a reaction product derived from reaction of a polyamine or a polyalkyleneimine and a substituted alkyl trialkyl quaternary ammonium salt. Also provided are surfactant compositions. The compositions may also include carriers, such as water, methanol, ethanol, propanol, isopropanol, butanol, isobutanol, monoethyleneglycol, an ethyleneglycol monobutyl ether, and hexylene glycol.

26 Claims, 8 Drawing Sheets

(56) References Cited

U.S. PATENT DOCUMENTS

| | | |
|---|---|---|
| 2006/0013798 A1 | 1/2006 | Henry et al. |
| 2006/0180794 A1 | 8/2006 | Goddard et al. |
| 2008/0286225 A1 | 11/2008 | Schonemyr et al. |
| 2009/0176887 A1 | 7/2009 | Vlasaty et al. |
| 2010/0280203 A1 | 11/2010 | Feuerhake et al. |
| 2011/0166236 A1 | 7/2011 | Tangestani-Nejad et al. |
| 2011/0177145 A1 | 7/2011 | Erkenbrecher, Jr. et al. |
| 2013/0011357 A1 | 1/2013 | Molenda et al. |
| 2015/0351383 A1 | 12/2015 | Kolari et al. |
| 2015/0352029 A1 | 12/2015 | Tokunaga et al. |
| 2015/0361276 A1 | 12/2015 | Mahmoud |
| 2016/0000690 A1 | 1/2016 | Tokunaga et al. |
| 2016/0068476 A1 | 3/2016 | Moonen et al. |
| 2016/0095876 A1 | 4/2016 | Salamone et al. |
| 2016/0143275 A1 | 5/2016 | Lan et al. |
| 2016/0249606 A1 | 9/2016 | Hartgrove et al. |

FOREIGN PATENT DOCUMENTS

| | | | |
|---|---|---|---|
| CN | 102631954 A | | 8/2012 |
| CN | 102887989 A | | 1/2013 |
| CN | 102924299 A | | 2/2013 |
| CN | 103113872 A | | 5/2013 |
| CN | 103464050 A | | 12/2013 |
| CN | 103483550 A | | 1/2014 |
| CN | 10-3936603 A | * | 7/2014 |
| CN | 103936603 A | | 7/2014 |
| CN | 104957133 A | | 10/2015 |
| CN | 105010387 A | | 11/2015 |
| CN | 105037176 A | | 11/2015 |
| CN | 105038738 A | | 11/2015 |
| CN | 105104399 A | | 12/2015 |
| CN | 104479169 B | | 3/2017 |
| EP | 0803498 A1 | | 10/1997 |
| EP | 2468713 A1 | | 6/2012 |
| GB | 2085433 A | | 4/1982 |
| GB | 2160538 A | | 12/1985 |
| JP | S 5430109 A | | 3/1979 |
| JP | S 62238337 A | | 10/1987 |
| JP | H 02216297 A | | 8/1990 |
| JP | H 0551352 A | | 3/1993 |
| JP | H 08188560 A | | 7/1996 |
| JP | 2002317193 A | | 10/2002 |
| JP | 4057796 B2 | | 3/2008 |
| JP | 2008222761 A | | 9/2008 |
| JP | 2009067699 A | | 4/2009 |
| JP | 2011132284 A | | 7/2011 |
| NO | 20003151 A | | 12/2000 |
| WO | WO 2000/039241 A1 | | 7/2000 |
| WO | WO 2005/097732 A1 | | 10/2005 |
| WO | WO 2011/084996 A2 | * | 7/2011 |
| WO | WO 2011084996 A2 | | 7/2011 |
| WO | WO 2013/077855 A1 | | 5/2013 |
| WO | WO 2014/008379 A2 | | 1/2014 |
| WO | WO 2014/098871 A2 | | 6/2014 |
| WO | WO 2014/107329 A1 | * | 7/2014 |
| WO | WO 2014107329 A1 | | 7/2014 |
| WO | WO 2016/105338 A1 | | 6/2016 |

OTHER PUBLICATIONS

Kim, Tae-Seong et al., "Preparation and Properties of Multiple Ammonium Salts Quaternized by Epichlorohydrin," Langmuir (1996) 12: 6304-6308.

Li, Jie et al., "Synthesis and Properties of the Dendritic Tetrameric Surfactants," Advanced Materials Research (2011) 183-185: 1667-1671.

Mei, Ping et al, "Synthesis of cationic gemini surfactants of special functional groups," Chemical Engineer (2008) 154(7): 31-33, 45 (English Abstract on first page).

Miao, Zong Cheng et al., "Preparation of Novel Gemini Quaternary Ammonium Salt Cationic Surfactant," Applied Mechanics and Materials (2012) 174-177: 1433-1436.

Raymond, Jon et al., "Determining Effective Antimicrobial Treatments for Long-Term Protection of Hydrocarbon Reservoirs," NACE—International Corrosion Conference Series, 2014, Paper No. 3879: 1-15.

Sao, Ikeda, et al, "Synthesis and Properties of Novel Germini Cationic Surfactants (II)—Multiple Quaternary Ammonium Salts from Dodecylamine and Epichlorohydrin," China Surfactant Detergent & Cosmetics (2001) 31(4): 36-38 (English Abstract on last page).

Timofeeva, Larisa M. et al., "Nonquaternary poly(diallylammonium) polymers with different amine structure and their biocidal effect on *Mycobacterium tuberculosis* and *Mycobacterium smegmatis*," Applied Microbiology Biotechnology (2015) 99(6): 2557-2575.

Wang, Dong et al., "Multiple-stimulus-responsive hydrogels of cationic surfactants and azoic salt mixtures," Colloid and Polymer Science (2013) 291(12) 2935-2946.

Yoshimura, Tomokazu et al., "Star-Shaped Trimeric Quaternary Ammonium Bromide Surfactants: Adsorption and Aggregation Properties," Lagnmuir (2012) 28: 9322-9331.

Yudovin-Farber, Ira et al., "Quaternary Ammonium Polyethyleneimine: Antibacterial Activity," Journal of Nanomaterials, vol. 2010, Article ID 826343: 1-11.

Zhang, Feng et al., "Preparation and Properties of Amino-Terminated Hyperbranched Polymers and Its Quaternary Ammonium Salt," Polymer Materials Science and Engineering, (Aug. 2009) 25(8): 141-144. (English Abstract on last page.).

PCT International Search Report and Written Opinion for PCT/US2017/065873, dated Mar. 19, 2018, 16 pages.

International Search Report and Written Opinion for PCT/US2019/035984. dated Jul. 30, 2019; 12 pages.

* cited by examiner

QUATERNARY CATIONIC POLYMERS

FIELD OF THE INVENTION

This disclosure generally relates to cationic polymer salts, and more particularly to compositions to be used as surfactants, antimicrobial compounds, and corrosion inhibitors.

BACKGROUND

Quaternary ammonium compounds comprise an important subcategory of surfactants because they contain unique properties. A main distinction between quaternary ammonium compounds and other surfactants is their unique structure. Quaternary ammonium compounds consist mainly of two moieties, a hydrophobic group, e.g., long alkyl group, and a quaternary ammonium salt group. The unique positive charge of the ammonium plays a key role, i.e., electrostatic interactions, between the surfactant and surface.

Industrial water systems employ process water to serve many different purposes but may be prone to microbial contamination and fouling. Fouling or deposition of any organic or inorganic material can occur even in industrial water systems treated with the best water treatment programs currently available.

If these industrial water systems are not periodically cleaned, then they will become heavily fouled. Fouling has a negative impact on the industrial water system. For example, severe mineral scale (inorganic material) will buildup on the water contact surfaces and anywhere there is scale providing an ideal environment for microorganism growth.

Evaporative cooling water systems are particularly prone to fouling. This fouling occurs by a variety of mechanisms including deposition of air-borne, water-borne, or water-formed contaminants; water stagnation; process leaks; and other factors. If allowed to progress, the system can suffer from decreased operational efficiency, premature equipment failure, and increased health-related risks associated with microbial fouling.

Fouling can also occur due to microbiological contamination. Sources of microbial contamination in industrial water systems are numerous and may include, but are not limited to, air-borne contamination, water make-up, process leaks and improperly cleaned equipment. These microorganisms can establish microbial communities on any wetable or semi-wetable surface of the water system.

Exopolymeric substances secreted by microorganisms aid in the formation of biofilms as the microbial communities develop on surfaces. These biofilms are complex ecosystems that establish a means for concentrating nutrients and offer protection for growth, and biofilms can accelerate scale, corrosion, and other fouling processes. Not only do biofilms contribute to reduction of system efficiencies, but they also provide an excellent environment for microbial proliferation that can include *Legionella* bacteria. It is therefore important that biofilms and other fouling processes be reduced to the greatest extent possible to minimize the health-related risk associated with *Legionella* and other water-borne pathogens.

Corrosion inhibitors are often added into upstream oil and gas production fluids to protect carbon steel pipelines and infrastructure from corrosion. Quaternary ammonium compounds have been used for many years as part of corrosion inhibitor formulations but are most often are bis quaternary species or species quaternized with benzyl chloride, which is known to be very hazardous.

There is a continuing need for quaternary ammonium compounds that fill this niche of surfactants and corrosion inhibitors.

BRIEF SUMMARY

In some embodiments, a cationic polymer salt is provided which comprises a reaction product derived from a reaction of a polyamine or a polyalkyleneimine and a substituted alkyl trialkyl quaternary ammonium salt.

In certain embodiments, the present disclosure provides a cationic polymer salt comprising a reaction product derived from a reaction of a polyamine or a polyalkyleneimine and a substituted alkyl trialkyl quaternary ammonium salt of formula (I):

wherein each $X^-$ is independently an anion; $R_1$ is $C_1$-$C_6$ alkylene substituted with hydroxyl or —$OR_5$ and an $X^-$ end group; $R_2$, $R_3$, and $R_4$ are each independently $C_1$-$C_{22}$ alkyl or $C_7$-$C_{22}$ arylalkyl; and $R_5$ is $C_1$-$C_6$ alkyl.

In some embodiments, a cationic polymer salt is provided which comprises formula (III):

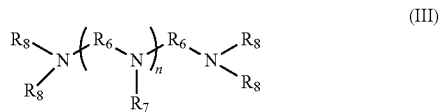

wherein each $R_6$ is independently $C_2$-$C_6$ alkylene; each $R_7$ is independently hydrogen, —$R_8$, —$R_6$—$N(R_8)_2$, —$R_6$—$N(R_8)$—$R_6$—$N(R_8)_2$, or —$R_6$—$N$—$(R_6$—$N(R_8)_2)_2$; each $R_8$ is independently hydrogen or

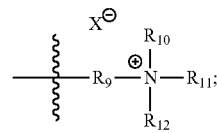

each $R_9$ is independently $C_2$-$C_6$ alkylene substituted with hydroxyl or –$OR_{13}$; $R_{10}$, $R_{11}$, and $R_{12}$ are each independently $C_1$-$C_{22}$ alkyl or $C_7$-$C_{22}$ arylalkyl; $R_{13}$ is $C_1$-$C_6$ alkyl; n is an integer from 1 to 100; and each $X^-$ is independently an anion.

In some embodiments, a cationic polymer salt is provided which comprises a reaction product derived from a reaction of a polyamine, an alkyleneimine, or a polyalkyleneimine and a substituted alkyl trialkyl quaternary ammonium salt of formula (I):

wherein each $X^-$ is independently an anion; $R_1$ is $C_1$-$C_6$ alkylene substituted with a hydroxyl or —$OR_5$ and an $X^-$ end group; $R_2$, $R_3$, and $R_4$ are each independently $C_1$-$C_{22}$ alkyl or $C_7$-$C_{22}$ arylalkyl; and $R_5$ is $C_1$-$C_6$ alkyl; and wherein any one of the following:

(A) the cationic polymer salt has no substitutions within its main chain, no alkyl-quaternized ammonium within its main chain, and comprises at least 4 quaternary ammonium groups; or (B) the cationic polymer salt has one or more terminal tertiary amine groups having the formula (IV):

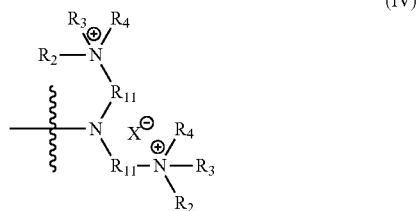

(IV)

wherein $R_{11}$ is $R_1$ without the $X^-$ end group, and either: the polymer salt has no substitutions within its main chain or at least 1 of $R_2$, $R_3$, and $R_4$ is a $C_9$-$C_{22}$ alkyl group; or (C) $R_2$ and $R_3$ are $C_6$-$C_{22}$ alkyl or $C_7$-$C_{22}$ arylalkyl and $R_4$ is methyl.

In some embodiments, a method for controlling microbes in an aqueous system is disclosed. The method can include adding to the aqueous system a reaction product derived from a reaction of a polyamine or a polyalkyleneimine and a substituted alkyl trialkyl quaternary ammonium salt of formula (I):

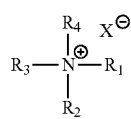

(I)

wherein each $X^-$ is independently an anion; $R_1$ is $C_1$-$C_6$ alkylene substituted with a hydroxyl or –$OR_5$ and an $X^-$ end group; $R_2$, $R_3$, and $R_4$ are each independently $C_1$-$C_{22}$ alkyl or $C_7$-$C_{22}$ arylalkyl; and $R_5$ is $C_1$-$C_6$ alkyl.

In some embodiments of the present disclosure, a method is disclosed for controlling microbes in process water by adding a composition to the process water. The composition may include a cationic polymer of formula (III):

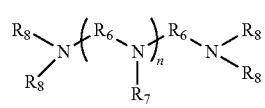

(III)

where each $R_6$ may be independently $C_2$-$C_6$ alkylene; each $R_7$ may be independently hydrogen, —$R_8$, —$R_6$—$N(R_8)_2$, —$R_6$—$N(R_8)$—$R_6$—$N(R_8)_2$, or —$R_6$—$N$—$(R_6$—$N(R_8)_2)_2$; each $R_8$ may be independently hydrogen or

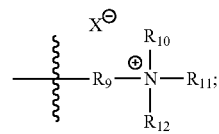

each $R_9$ may be independently $C_2$-$C_6$ alkylene substituted with hydroxyl or —$OR_{13}$; $R_{10}$, $R_{11}$, and $R_{12}$ are each independently $C_1$-$C_{22}$ alkyl or $C_7$-$C_{22}$ arylalkyl; $R_{13}$ may be $C_1$-$C_6$ alkyl; n may be an integer from 1 to 100; and each $X^-$ may be independently an anion.

In some embodiments, a method is provided for controlling microbes on a surface by adding a composition to the surface. The composition may include a cationic polymer of formula (III):

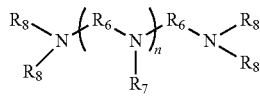

(III)

where each $R_6$ may be independently $C_2$-$C_6$ alkylene; each $R_7$ may be independently hydrogen, —$R_8$, —$R_6$—$N(R_8)_2$, —$R_6$—$N(R_8)$—$R_6$—$N(R_8)_2$, or —$R_6$—$N$—$(R_6$—$N(R_8)_2)_2$; each $R_8$ may be independently hydrogen or

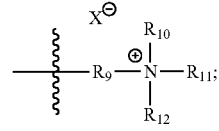

each $R_9$ may be independently $C_2$-$C_6$ alkylene substituted with hydroxyl or —$OR_{13}$; $R_{10}$, $R_{11}$, and $R_{12}$ are each independently $C_1$-$C_{22}$ alkyl or $C_7$-$C_{22}$ arylalkyl; $R_{13}$ may be $C_1$-$C_6$ alkyl; n may be an integer from 1 to 100; and each $X^-$ may be independently an anion.

In some embodiments, a method of inhibiting corrosion on a surface is disclosed. The method can include contacting the surface with a reaction product derived from a reaction of a polyamine or a polyalkyleneimine and a substituted alkyl trialkyl quaternary ammonium salt of formula (I):

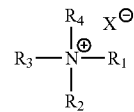

(I)

wherein each $X^-$ is independently an anion; $R_1$ is $C_1$-$C_6$ alkylene substituted with a hydroxyl or —$OR_5$ and an $X^-$ end group; $R_2$, $R_3$, and $R_4$ are each independently $C_1$-$C_{22}$ alkyl or $C_7$-$C_{22}$ arylalkyl; and $R_5$ is $C_1$-$C_6$ alkyl.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE DRAWINGS

A detailed description of the invention is hereafter described with specific reference being made to the drawings in which.

DETAILED DESCRIPTION

Figure 1:
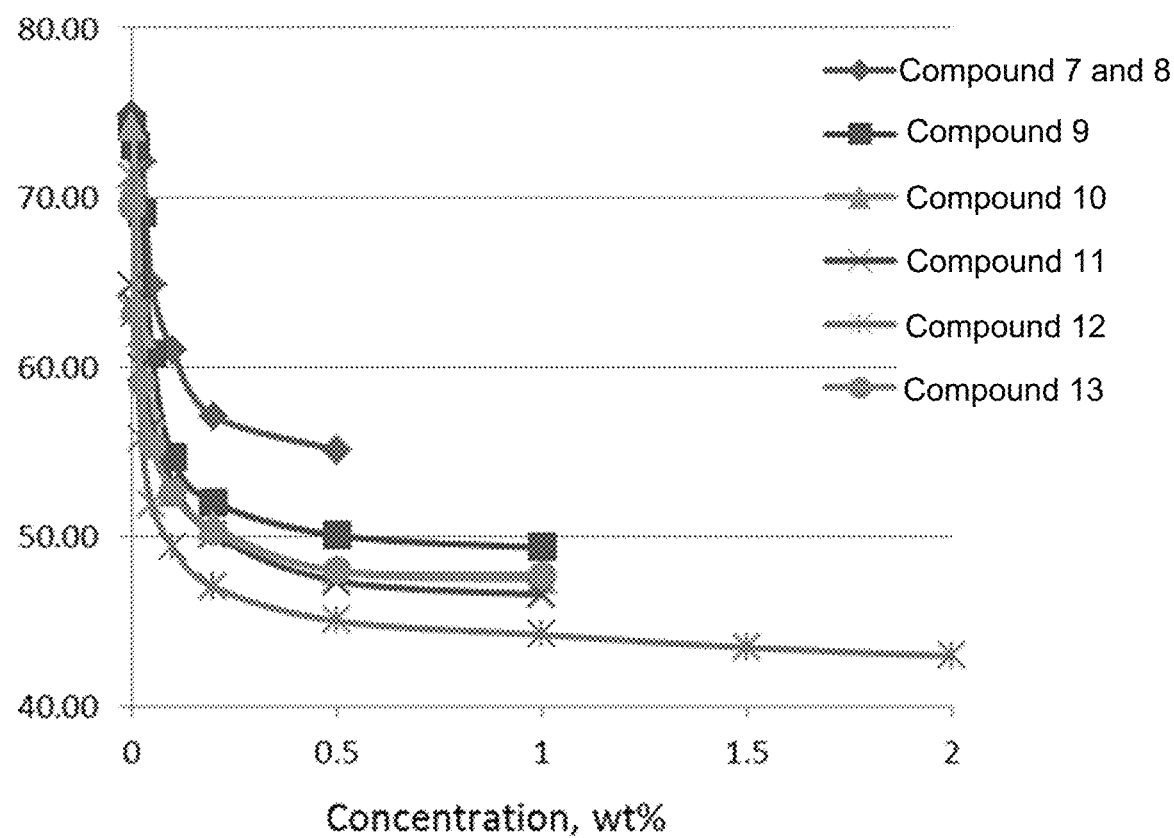
FIG. 1 shows a graph of surface-tension (mN/m) vs. concentration (wt %) of various quaternary cationic surfactants.

The present application discloses cationic polymer salts which comprise a reaction product derived from a reaction of a polyamine, an alkyleneimine, or a polyalkyleneimine and a substituted alkyl trialkyl quaternary ammonium salt. Newly synthesized antimicrobial and anticorrosion cationic polymer salts with multiple quaternary groups are disclosed herein and may be particularly useful, for example, in controlling microbial populations or inhibiting corrosion in process water used in industrial systems. The disclosed compounds show antimicrobial and anticorrosion activity and may be used in any application requiring control of microbes or corrosion inhibition.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only, and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional steps or components. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

Unless otherwise indicated, an "alkyl" group as described herein alone or as part of another group is an optionally substituted linear saturated monovalent hydrocarbon radical containing from one to thirty-two carbon atoms, or an optionally substituted branched saturated monovalent hydrocarbon radical containing three to thirty-two carbon atoms. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like. Alkyl groups can be unsubstituted or substituted by one or more suitable substituents, as defined below. Preferably, the substitutions are not within the main chain or backbone of the polymer salt.

"Arylalkyl" means an aryl group attached to the parent molecule through an alkylene group. The number of carbon atoms in the aryl group and the alkylene group is selected such that there is a total of about 7 to about 22 carbon atoms in the arylalkyl group. A preferred arylalkyl group is benzyl.

The term "-ene" as used as a suffix as part of another group denotes a bivalent radical in which a hydrogen atom is removed from each of two terminal carbons of the group. For example, alkylene denotes a bivalent alkyl group such as methylene ($-CH_2-$) or ethylene ($-CH_2CH_2-$). For clarity, addition of the -ene suffix is not intended to alter the definition of the principal word other than denoting a bivalent radical. Thus, continuing the example above, alkylene denotes an optionally substituted linear saturated bivalent hydrocarbon radical.

The term "suitable substituent," as used herein, is intended to mean a chemically acceptable functional group that does not negate the activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, arylalkyl or heteroarylalkyl groups, arylalkoxy or heteroarylalkoxy groups, carboxyl groups, heterocyclic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, and arylsulfonyl groups. Those skilled in the art will appreciate that many substituents can be substituted by additional substituents.

The cationic polymer salts of the present disclosure exhibit reduced surface tension in aqueous solution with increasing numbers of alkyl chains in the molecule, and are useful as cationic surfactants or foaming agents (e.g., for use in cleaning formulations or personal care products, such as shampoos). The cationic polymer salts have multiple alkyl chains and multiple hydrophilic groups which provide unexpected physicochemical properties in comparison with conventional amphiphilic compounds having one alkyl chain and one hydrophilic group.

In some embodiments, the substituted alkyl trialkyl quaternary ammonium salt monomer comprises formula (I):

wherein each $X^-$ is independently an anion; $R_1$ is $C_1$-$C_6$ alkylene substituted with hydroxyl or —$OR_5$ and an $X^-$ end group; $R_2$, $R_3$, and $R_4$ are each independently $C_1$-$C_{22}$ alkyl or $C_7$-$C_{22}$ arylalkyl; and $R_5$ is $C_1$-$C_6$ alkyl.

$R_1$ can comprise $C_2$-$C_3$ alkylene substituted with hydroxyl and having an $X^-$ end group.

Suitable $X^-$ anions can include, but are not limited to, chloride, bromide, fluoride, iodide, acetate, aluminate, cyanate, cyanide, dihydrogen phosphate, dihydrogen phosphite, formate, hydrogen carbonate, hydrogen oxalate, hydrogen sulfate, hydroxide, metaniobate, metavanadate, nitrate, nitrite, thiocyanate, or a combination thereof. In some embodiments, the anion can comprise chloride or bromide.

$R_2$, $R_3$, and $R_4$ can be independently $C_1$-$C_{22}$ alkyl. In some embodiments, $R_2$, $R_3$, and $R_4$ can all be methyl. Alternatively, $R_2$ can be $C_6$-$C_{22}$ alkyl or $C_7$-$C_{22}$ arylalkyl and $R_3$ and $R_4$ can be $C_1$-$C_4$ alkyl such as methyl, or $R_2$ and $R_3$ are $C_6$-$C_{22}$ alkyl or $C_7$-$C_{22}$ arylalkyl and $R_4$ is $C_1$-$C_4$ alkyl such as methyl.

Suitable substituted alkyl trialkyl quaternary ammonium salt monomers can include, but not limited to, 3-chloro-2-hydroxypropyl-trimethylammonium chloride; 3-chloro-2-hydroxypropyl-dodecyl-dimethylammonium chloride; 3-chloro-2-hydroxypropyl-stearyl-dimethylammonium chloride; or a combination thereof.

The polyamine can comprise a polymer of formula (II):

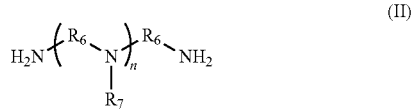

(II)

wherein n is an integer from 0 to 100; each $R_6$ is independently $C_2$-$C_6$ alkylene; and each $R_7$ is independently hydrogen or —$R_6$—$NH_2$, —$R_6$—NH—$R_6$—$NH_2$, or —$R_6$—N—($R_6$—$NH_2$)$_2$.

In the polyamine of formula (II), n can be from 0 to 90, 0 to 80, 0 to 70, 0 to 60, 0 to 50, 0 to 45, 0 to 40, 0 to 35, 0 to 30, 0 to 25, 0 to 20, 0 to 15, 0 to 10, 0 to 9, 0 to 8, 0 to 7, 0 to 6, 0 to 5, 1 to 90, 1 to 80, 1 to 70, 1 to 60, 1 to 50, 1 to 45, 1 to 40, 1 to 35, 1 to 30, 1 to 25, 1 to 20, 1 to 15, 1 to 10, 1 to 9, 1 to 8, 1 to 7, 1 to 6, 1 to 5. In some embodiments, n may be from 2 to 5, 2 to 6, 2 to 7, 2 to 8, 2 to 9, 2 to 10, 2 to 25, 2 to 30, 2 to 35, 2 to 40, 2 to 45, 2 to 90, or any sub-range thereof. In other embodiments, n may be from 3 to 100, 3 to 90, 3 to 80, 3 to 70, 3 to 60, 3 to 50, 3 to 45, 3 to 40, 3 to 35, 3 to 30, 3 to 25, 3 to 10, or any sub-range thereof. In certain embodiments, n is selected from 1, 2, 3, 4, 5, 6, 7, 8, 9, or 10.

In the polyamine of formula (II), $R_6$ can be $C_2$-$C_3$ alkyl. In some embodiments, $R_6$ can be ethyl.

In the polyamine of formula (II), none of the nitrogens of the polyamine need be quaternized.

Suitable polyamines can include an alkyleneamine. The alkyleneamine can comprise, but is not limited to, ethylenediamine, diethylenetriamine, triethylenetetraamine, diethylenetriamine, triethylenetetramine, tetraethylenepentamine, pentaethylenehexamine, hexaethyleneheptamine, or a combination thereof.

Suitable polyalkyleneimines can include, but are not limited to, ethyleneimine, propyleneimine, butyleneimine, pentyleneimine, hexyleneimine, heptyleneimine, or a combination thereof.

Suitable polyalkyleneimines can include, but are not limited to, branched, linear, or dendrimer polyethyleneimines.

In some embodiments, the weight average molecular weight of the linear, branched, or dendrimer polyethyleneimine, as measured by gel permeation chromatography, may range from about 200 gm/mol to about 750,000 gm/mol. In some embodiments, the weight average molecular weight of the polymeric salt may be about 800 gm/mol, about 1,300 gm/mol, about 2,000 gm/mol, about 5,000 gm/mol, about 20,000 gm/mol, about 25,000 gm/mol, or about 750,000 gm/mol.

In some embodiments, the viscosity of the linear, branched, or dendrimer polyethyleneimine, as measured according to ISO 2555 on a Brookfield viscometer, may range from about 100 mPa·s to about 30,000 mPa·s. In some embodiments, the viscosity of the linear, branched, or dendrimer polyethyleneimine, may range from about 200 mPa·s to about 15,000 mPa·s or from about 200 mPa·s to about 500 mPa·s. In some embodiments, the viscosity of the linear, branched, or dendrimer polyethyleneimine, may be about 300 mPa·s, about 400 mPa·s, about 500 mPa·s, about 600 mPa·s, or about 1000 mPa·s.

In some embodiments, the ratio of the primary amine/secondary amine/tertiary amine in the polyethyleneimine may be about 1/0.9/0.6 as measured by $^{13}$CNMR. The amount of amine in the dry polyethyleneimine may range from about 10 mmol/gm to about 30 mmol/gm. The amount of amine in the polyethyleneimine may be about 12 mmol/gm, about 13 mmol/gm, about 14 mmol/gm, about 15 mmol/gm, about 16 mmol/gm, about 17 mmol/gm, about 18 mmol/gm, about 19 mmol/gm, about 20 mmol/gm, about 21 mmol/gm, or about 22 mmol/gm.

The molar ratio of the polyamine or polyalkyleneimine to the substituted alkyl trialkyl quaternary ammonium salt as reactants can range from 1:1 to 1:100, 1:1 to 1:90, 1:1 to 1:80, 1:1 to 1:70, 1:1 to 1:60, 1:1 to 1:50, 1:1 to 1:45, 1:1 to 1:40, 1:1 to 1:35, 1:1 to 1:30, 1:1 to 1:25, 1:1 to 1:20, 1:1 to 1:15, 1:1 to 1:10, 1:1 to 1:9, 1:1 to 1:8, 1:1 to 1:7, 1:1 to 1:6, 1:1 to 1:5, 1:1 to 1:4, 1:1 to 1:3, or 1:1 to 1:2.

In some embodiments, a cationic polymer salt is provided which comprises a reaction product derived from a reaction of a polyamine, an alkyleneimine, or a polyalkyleneimine and the substituted alkyl trialkyl quaternary ammonium salt of formula (I) as described above, and wherein any one of the following:

(A) the cationic polymer salt has no substitutions within its main chain, no alkyl-quaternized ammonium within its main chain, and comprises at least 4 quaternary ammonium groups; or (B) the cationic polymer salt has one or more terminal tertiary amine groups having the formula (IV):

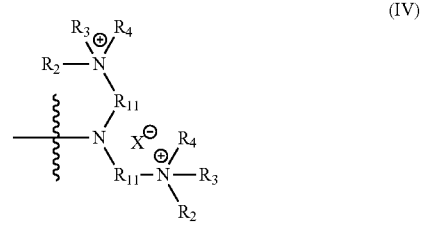

(IV)

wherein $R_{11}$ is $R_1$ without the $X^-$ end group, and either: the polymer salt has no substitutions within its main chain or at least 1 of $R_2$, $R_3$, and $R_4$ is a $C_9$-$C_{22}$ alkyl group; or (C) $R_2$ and $R_3$ of formula (I) are $C_6$-$C_{22}$ alkyl or $C_7$-$C_{22}$ arylalkyl and $R_4$ is methyl.

In some embodiments, the cationic polymer salt can comprise a polymer of formula (III):

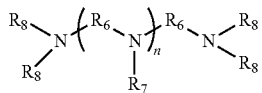
(III)

wherein each $R_6$ is independently $C_2$-$C_6$ alkylene; each $R_7$ is independently hydrogen, —$R_8$, —$R_6$—N($R_8$)$_2$, —$R_6$—N($R_8$)—$R_6$—N($R_8$)$_2$, or —$R_6$—N—($R_6$—N($R_8$)$_2$)$_2$; each $R_8$ is independently hydrogen or

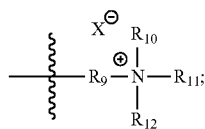

each $R_9$ is independently $C_2$-$C_6$ alkylene substituted with hydroxyl or –$OR_{13}$; $R_{10}$, $R_{11}$, and $R_{12}$ are each independently $C_1$-$C_{22}$ alkyl or $C_7$-$C_{22}$ arylalkyl; $R_{13}$ is $C_1$-$C_6$ alkyl; n is an integer from 1 to 100; and each $X^-$ is independently an anion.

Also provided is a cationic polymer salt having the formula (V):

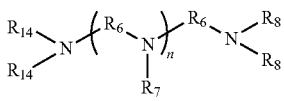
(V)

wherein $R_6$, $R_7$, $R_8$, $R_9$, $R_{10}$, $R_{11}$, $R_{12}$, $R_{13}$, n, and $X^-$ are as defined for formula (III) above, $R_{14}$ is

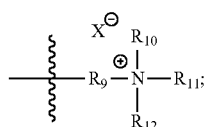

and wherein one of the following:
(a) the polymer salt has no substitutions within its main chain, no alkyl-quaternized ammonium within its main chain, and comprises at least 4 quaternary ammonium groups; or
(b) either: the polymer salt has no substitutions within its main chain or at least 1 of $R_{10}$, $R_{11}$, and $R_{12}$ of $R_{14}$ is a $C_9$-$C_{22}$ alkyl group; or
(c) the polymer salt includes at least 3 of $R_{12}$ wherein $R_{12}$ is $C_9$-$C_{15}$ alkyl; or
(d) the polymer salt includes at least 3 of $R_{12}$ wherein $R_{12}$ is $C_{15}$-$C_{22}$ alkyl.

In the polymer salt of formula (III) or (V), n can be from 1 to 90, 1 to 80, 1 to 70, 1 to 60, 1 to 50, 1 to 45, 1 to 40, 1 to 35, 1 to 30, 1 to 25, or any sub-range thereof. In some embodiments, n may be from 2 to 25, 2 to 30, 2 to 35, 2 to 40, 2 to 45, 2 to 90, or any sub-range thereof. In other embodiments, n may be from 3 to 100, 3 to 90, 3 to 80, 3 to 70, 3 to 60, 3 to 50, 3 to 45, 3 to 40, 3 to 35, 3 to 30, 3 to 25, or any sub-range thereof. In certain embodiments, n is selected from 1, 2, 3, 4, 5, 6, 7, 8, 9, or 10.

In the polymer salt of formula (III) or (V), each $R_6$ and $R_9$ can be independently $C_2$-$C_3$ alkylene. In some embodiments, each $R_6$ can be ethylene.

In the polymer salt of formula (III), each $R_9$ can be hydroxypropylene; $R_{10}$ and $R_{11}$ can be methyl; and each $R_{12}$ can be independently methyl or $C_8$-$C_{22}$ alkyl. In some embodiments, at least one $R_{12}$ is $C_8$-$C_{22}$ alkyl.

In other embodiments of the polymer salt of formula (III), $R_7$ is —$R_8$, —$R_6$—N($R_8$)$_2$, —$R_6$—N($R_8$)—$R_6$—N($R_8$)$_2$, or —$R_6$—N—($R_6$—N($R_8$)$_2$)$_2$; each $R_8$ is

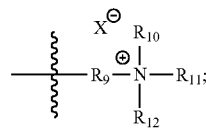

each $R_9$ is independently $C_2$-$C_6$ alkylene substituted with hydroxyl or —$OR_{13}$; $R_{10}$, $R_{11}$, and $R_{12}$ are each independently $C_1$-$C_{22}$ alkyl or $C_7$-$C_{22}$ arylalkyl; $R_{13}$ is $C_1$-$C_6$ alkyl; n is an integer from 1 to 100; and each $X^-$ is independently an anion.

In some embodiments of the polymer salt of formula (III), at least one of $R_{12}$ may be a saturated $C_9$-$C_{15}$ alkyl group. The saturated alkyl group may range from $C_{10}$ to $C_{15}$, $C_{11}$ to $C_{15}$, $C_{12}$ to $C_{15}$, $C_{12}$ to $C_{14}$, $C_{11}$ to $C_{14}$, $C_{10}$ to $C_{14}$, $C_9$ to $C_{14}$, $C_9$ to $C_{13}$, $C_{10}$ to $C_{13}$, or $C_{11}$ to $C_{13}$. In other embodiments at least 2, 3, 4, or 5 of $R_{12}$ may be a saturated $C_9$-$C_{15}$ alkyl group. For instance, at least one of $R_{12}$ may be a $C_{12}$ alkyl group, or, at least 2, 3, 4, or 5 of $R_{12}$ may be a $C_{12}$ alkyl group.

In other embodiments of the polymer salt of formula (III), at least one of $R_{12}$ may be a saturated $C_{15}$-$C_{22}$ alkyl group. The saturated alkyl group may range from $C_{16}$ to $C_{22}$, $C_{17}$ to $C_{21}$, $C_{16}$ to $C_{20}$, $C_{18}$ to $C_{22}$, $C_{16}$ to $C_{18}$, $C_{15}$ to $C_{18}$, $C_{15}$ to $C_{20}$, or $C_{17}$ to $C_{19}$. In other embodiments, at least 2, 3, 4, or 5 of $R_{12}$ may be a saturated $C_{15}$-$C_{22}$ alkyl group.

In other embodiments, at least one of $R_{12}$ may be a saturated $C_{12}$ alkyl group. In still further embodiments, at least 2, 3, 4, or 5 of $R_{12}$ may be a saturated $C_{12}$ alkyl group.

In other embodiments, at least one of $R_{12}$ may be a saturated $C_{18}$ alkyl group. In still further embodiments, at least 2, 3, 4, or 5 of $R_{12}$ may be a saturated $C_{18}$ alkyl group.

In some embodiments of the polymer salt of formula (III), at least one $R_9$ can be $R_8$, or at least two, three or four $R_9$ can be $R_8$. In some embodiments, the cationic salt of formula (III) may comprise at least three substituted alkyl trialkyl quaternary ammonium groups. In other embodiments, there may be at least four, five, or six quaternary ammonium groups. In some embodiments, the quaternary ammonium groups may not be in the main chain or backbone of the polymer salt, but only on the branches or side-chains.

In any of the polymer salts as described herein, the polymer salt may not have any alkyl-quaternary ammoniums within the main chain of the polymer salt. For example, the polymer salt may not have any —N(CH$_3$)(CH$_3$)— nitrogens within the main chain of the polymer salt. In addition, the polymer salt may not have any substitutions within the main chain (i.e. backbone) of the polymer salt.

In certain embodiments, the composition of the cationic polymer may further include a carrier. In some embodiments, a surfactant composition is provided and the surfactant composition may comprise a cationic polymer salt and a carrier, such as an aqueous carrier.

Suitable carriers can include, but are not limited to, water, an alcohol, an aromatic hydrocarbon, an alkylene glycol, an alkyleneglycol alkyl ether, or a combination thereof. For example, suitable carriers include methanol, ethanol, propanol, isopropanol, butanol, isobutanol, monoethyleneglycol, ethyleneglycol monobutyl ether, hexylene glycol or a combination thereof.

The preparation of cationic polymer salts can be conducted conveniently by reacting a polyamine or a polyalkyleneimine or any combination thereof with a substituted alkyl trialkyl quaternary ammonium salt at a pH of at least about 7.5 to form the polymer salt. The molar ratio of the polyamine or polyalkyleneimine to the substituted alkyl trialkyl quaternary ammonium salt as reactants can range from 1:1 to 1:100, 1:1 to 1:90, 1:1 to 1:80, 1:1 to 1:70, 1:1 to 1:60, 1:1 to 1:50, 1:1 to 1:45, 1:1 to 1:40, 1:1 to 1:35, 1:1 to 1:30, 1:1 to 1:25, 1:1 to 1:20, 1:1 to 1:15, 1:1 to 1:10, 1:1 to 1:9, 1:1 to 1:8, 1:1 to 1:7, 1:1 to 1:6, 1:1 to 1:5, 1:1 to 1:4, 1:1 to 1:3, or 1:1 to 1:2. The reaction mixture can be stirred and heated to about 50-100° C. for about 2 to 6 hours. A base can be added to maintain a pH of at least about 7.5. For example, the reactants can be added to an aqueous solution in a reactor while monitoring the pH of the aqueous solution until the completion of reaction, and adjusting the pH of the aqueous medium to maintain the pH value of the aqueous solution equal to or greater than about 7.5.

For example, an alkyleneamine such as diethylenetriamine and a substituted alkyltrialkyl quaternary ammonium salt such as 3-chloro-2-hydroxypropyl trimethylammonium chloride can be added to a reaction container equipped with a mechanical stirrer, a thermometer, a temperature controller, a condenser, and an addition funnel. The reaction mixture is stirred and gently heated to about 60° C. The pH value of the reaction is continuously monitored. A base such as sodium hydroxide (50% aqueous solution) is slowly added to the reaction container and the temperature is held constant at about 60° C. The pH value of reaction solution is measured and held constant above about 7.5. The reaction temperature is raised to about 85° C. and held constant for about 5 hours.

As another example, a polyalkyleneimine such as polyethyleneimine and a substituted alkyltrialkyl quaternary ammonium salt such as 3-chloro-2-hydroxypropyl trimethylammonium chloride can be added to a reaction container equipped with a mechanical stirrer, a thermometer, a temperature controller, a condenser, and an addition funnel. The reaction mixture is stirred and gently heated to about 60° C. The pH value of the reaction is continuously monitored. A base such as sodium hydroxide (50% aqueous solution) is slowly added to the reaction container and the temperature is held constant at about 60° C. The pH value of reaction solution is measured and held constant above about 7.5. The reaction temperature is raised to about 85° C. and held constant for about 5 hours.

The polymer salts described herein are generally random polymers wherein the exact order of the structural units derived from the polyamine, polyalkyleneimine and substituted alkyl trialkyl quaternary ammonium salt is not predetermined.

The polymer salt is generally a reaction product of a mixture that may also contain components that are not chemically incorporated into the polymer. For those reaction products that contain additional components in the mixture that are not intended to be incorporated into the polymer, such additional components typically comprise solvents, pH adjusting agents, buffers, and/or other components known to those of skill in the art.

The cationic polymer salts as described herein can be used as cationic surfactants, and can be substituted for conventional quaternary ammonium cationic surfactants in conventional cleaners and other formulations.

In some embodiments, the weight average molecular weight of the cationic polymeric salts described herein, as measured by gel permeation chromatography, may range from about 200 gm/mol to about 1,000,000 gm/mol. In some embodiments, the weight average molecular weight of the polymeric salt may be from about 500 gm/mol to about 100,000 gm/mol, from about 500 gm/mol to about 50,000 gm/mol, from about 500 gm/mol to about 40,000 gm/mol, from about 500 gm/mol to about 30,000 gm/mol, from about 5,000 gm/mol to about 30,000 gm/mol, from about 10,000 gm/mol to about 30,000 gm/mol, from about 500 gm/mol to about 20,000 gm/mol, from about 500 gm/mol to about 10,000 gm/mol, or from about 500 gm/mol to about 5,000 gm/mol.

In some embodiments, a method is provided for controlling microbes on a surface or in process water that includes adding a composition to the surface or process water. The composition may include a cationic polymer of formula III, as shown above where each $R_6$ may be independently $C_2$-$C_6$ alkylene; each $R_7$ may be independently hydrogen, —$R_8$, —$R_6$—$N(R_8)_2$, —$R_6$—$N(R_8)$—$R_6$—$N(R_8)_2$, or —$R_6$—N—($R_6$—$N(R_8)_2)_2$; each $R_8$ may be independently hydrogen or

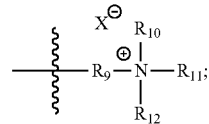

each $R_9$ may be independently $C_2$-$C_6$ alkylene substituted with hydroxyl or —$OR_{13}$; $R_{10}$, $R_{11}$, and $R_{12}$ are each independently $C_1$-$C_{22}$ alkyl or $C_7$-$C_{22}$ arylalkyl; $R_{13}$ may be $C_1$-$C_6$ alkyl; n may be an integer from 1 to 100; and each $X^-$ may be independently an anion.

In other embodiments, a method is provided for controlling microbes on a surface or in process water that includes adding a composition to the surface or process water. The composition may include a cationic polymer of formula III, as shown above, where each $R_6$ may be a $C_2$ alkylene; each $R_7$ may be independently —$R_8$, —$R_6$—$N(R_8)_2$, —$R_6$—N($R_8$)—$R_6$—$N(R_8)_2$, or —$R_6$—N—($R_6$—$N(R_8)_2)_2$; each $R_8$ may be

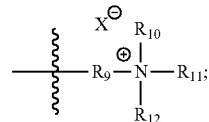

each $R_9$ may be independently $C_2$-$C_6$ alkylene substituted with hydroxyl or —$OR_{13}$; $R_{10}$, $R_{11}$, and $R_{12}$ are each independently $C_1$-$C_{22}$ alkyl or $C_7$-$C_{22}$ arylalkyl; $R_{13}$ may be $C_1$-$C_6$ alkyl; n may be an integer from 1 to 100; and each $X^-$ may be independently an anion.

In certain embodiments, the composition may include a mixture of different cationic polymer salts. In some embodiments, an antimicrobial composition is provided. The antimicrobial composition may comprise a cationic polymer salt of formula (III) and an aqueous carrier.

Suitable carriers can include, but are not limited to, water, an alcohol, an aromatic hydrocarbon, an alkylene glycol, an alkyleneglycol alkyl ether, or a combination thereof. For example, suitable carriers include methanol, ethanol, propanol, isopropanol, butanol, isobutanol, monoethyleneglycol, ethyleneglycol monobutyl ether, or a combination thereof.

In some embodiments, the composition added to the surface or process water may include a cationic polymer salt, such as Compound 1, Compound 2, Compound 3, or Compound 4.

Compound 1
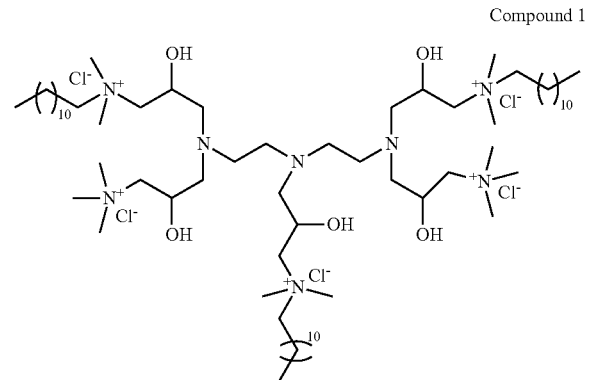

Compound 2
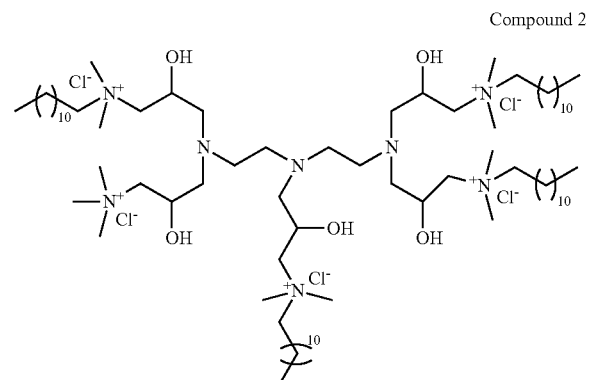

Compound 3
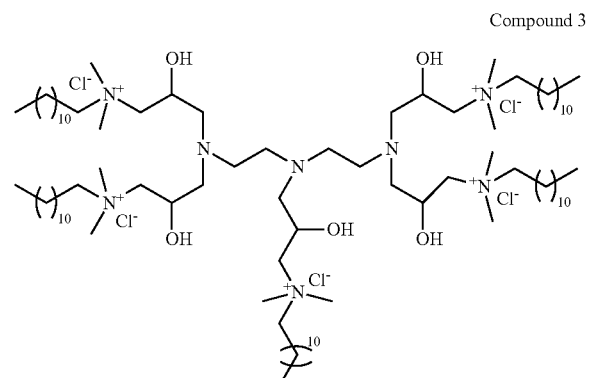

Compound 4
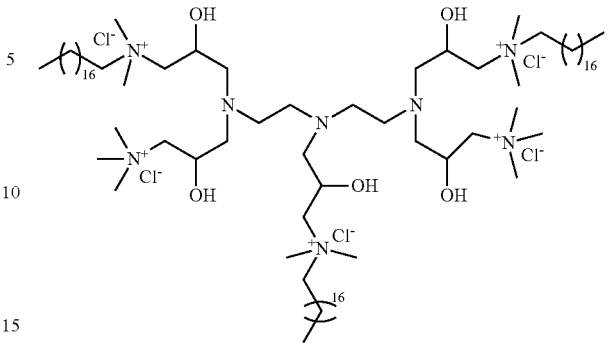

In some embodiments, the composition added to the surface or process water may include Compound 1. Compound 1 includes five quaternary amine groups, wherein four of the five comprise a saturated $C_{12}$ alkyl group.

In certain embodiments, the composition includes a biocide, a carrier, and cationic polymer salt selected from Compound 1, Compound 2, Compound 3, Compound 4, Compound 5, Compound 6, Compound 7, Compound 8, Compound 9, Compound 10, Compound 11, Compound 12, Compound 13, or any combination thereof. In certain embodiments, the composition includes a biocide, a carrier, and cationic polymer salt selected from Compound 14, Compound 15, or Compound 16. In some embodiments, the composition may consist of a cationic polymer salt of formula III. In some embodiments, the composition may consist of a cationic polymer salt of formula III and water. In some embodiments, the composition may consist of a cationic polymer salt of formula III, water, and a biocide.

Biocides suitable for use may be oxidizing or non-oxidizing biocides. Oxidizing biocides include, but are not limited to, bleach, chlorine, bromine, chlorine dioxide and materials capable of releasing chlorine and bromine. Non-oxidizing biocides include, but are not limited to, glutaraldehyde, isothiazolin, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, didecyl dimethyl ammonium chloride, poly(oxyethylene(dimethyliminio)ethylene(dimethyliminio)ethylene dichloride, methylene bisthiocyanate, 2-decylthioethanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis(tributyltin)oxide, 2-(tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo[2.2.1]heptane-2,3-dicarboxylic acid, 4,5-dichloro-2-n-octyl-4-isothiazoline-3-one, 5-chloro-2-methyl-4-isothiazolin-3-one and 2-methyl-4-isothiazolin-3-one.

In other embodiments, corrosion inhibitors may be added when needed to reduce corrosion of the metal in the industrial water system. Corrosion inhibitors for multi-metal protection are typically triazoles, such as, but not limited to, benzotriazole, halogenated triazoles, and nitro-substituted azoles.

In some embodiments, dispersants may be added to keep particulate matter present in the water of an industrial water system dispersed, so that it does not agglomerate and cause fouling during the cleaning and disinfecting process. Polymeric dispersants may be acrylic acid, polymaleic acid, copolymers of acrylic acid with sulfonated monomers and alkyl esters thereof. These polymers may include terpolymers of acrylic acid, acrylamide and sulfonated monomers. These polymers may also include quad-polymers consisting of acrylic acid and three other monomers.

In other embodiments, a method is provided for controlling microbes in process water or on a surface by adding to the process water or surface a composition that includes a cationic polymer salt of formula III. In other embodiments, the method may include adding a composition to the surface or process water that includes a cationic polymer salt of formula III, where n may be greater than 1 and each $R_7$ may be independently hydrogen, $-R_8$, $-R_6-N(R_8)_2$, $-R_6-N(R_8)-R_6-N(R_8)_2$, or $-R_6-N-(R_6-N(R_8)_2)_2$. The cationic polymer salt may be added to the surface or process water as an aqueous composition or as a dry powder. The cationic polymer salt may be added continuously or it may be added intermittently when more antimicrobial activity may be needed.

In other embodiments, the cationic polymer salt in the composition may be Compound 1, Compound 2, Compound 3, Compound 4, Compound 5, Compound 6, Compound 7, Compound 8, Compound 9, Compound 10, Compound 11, Compound 12, Compound 13, Compound 14, Compound 15, or any combination thereof. Chemical structures for Compounds 5-13 are shown below in the Examples.

In some embodiments, the cationic polymer salt may be added to the process water in an amount ranging from about 1 ppm to about 1000 ppm. In other embodiments, the amount of added cationic polymer salt in the process water may range from about 5 ppm to about 100 ppm, about 5 ppm to about 50 ppm, about 5 ppm to about 40 ppm, about 5 ppm to about 30 ppm, about 10 ppm to about 60 ppm, about 10 ppm to about 50 ppm, about 10 ppm to about 40 ppm, about 10 ppm to about 30 ppm, about 20 ppm to about 60 ppm, about 20 ppm to about 50 ppm, about 20 ppm to about 40 ppm, or about 20 ppm to about 30 ppm. In some embodiments, the cationic polymer salt may be added to the process water to an amount ranging from about 100 ppm to about 1000, about 125 to about 1000, about 250 to about 1000, or about 500 to about 1000.

In some embodiments, the method may be used to clean and disinfect surfaces or process water in any industrial water system. These industrial water system may include, but is not limited to cooling water systems, including open recirculating systems, closed and once-through cooling water systems, boilers and boiler water systems, petroleum well systems, downhole formations, geothermal wells and other oil field applications, mineral washing systems, flotation and benefaction systems, paper mill digesters, washers, bleach plants, stock chests, white water systems, paper machine surfaces, black liquor evaporators in the pulp industry, gas scrubbers and air washers, continuous casting processes in the metallurgical industry, air conditioning and refrigeration systems, industrial and petroleum process water, indirect contact cooling and heating water, water reclamation systems, water purification systems, membrane filtration water systems, food processing streams (meat, vegetable, sugar beets, sugar cane, grain, poultry, fruit and soybean), waste treatment systems, clarifiers, liquid-solid applications, municipal sewage treatment, municipal water systems, potable water systems, aquifers, water tanks, sprinkler systems, and water heaters.

In some embodiments, the industrial water system may cooling water systems, including open recirculating, closed and once-through cooling water systems, paper machine surfaces, food processing streams, waste treatment systems and potable water systems.

In still further embodiments, the method of treating process water may include the step of contacting a spore or a thermophile in the process water with the composition. The composition may partially inactivate or kill the spore or thermophile. In other embodiments, the method may include the step of contacting a bacterium in the process water with the composition. The composition may kill the bacterium or partially kill bacteria or microbes in the process water.

In another embodiment, the composition used in the method may include a biocide. The biocide may be any of those listed above or other known agent. The amount of biocide in the composition may be an effective amount that provides adequate control of the microbes in the process.

Another aspect of the invention is a composition for inhibiting corrosion at a surface. The composition comprises the cationic polymer salt as described herein and a component comprising an organic solvent, a corrosion inhibitor, an organic sulfur compound, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

The composition can comprise, for example, from about 0.1 to about 20 wt. % of one or more cationic polymer salts and from about 80 to about 99.9 wt. % of the component; from about 0.1 to about 20 wt. % of one or more cationic polymer salts, from about 1 to about 60 wt. % of the component and from about 20 to about 98.9 wt. % water; from about 10 to about 20 wt. % of one or more cationic polymer salts, from about 30 to about 40 wt. % of the component and from about 40 to about 60 wt. % water; or from about 15 to about 20 wt. % of one or more cationic polymer salts, from about 1 to about 10 wt. % of the component and from about 70 to about 84 wt. % water.

The component of the composition can comprise an organic solvent. The composition can comprise from about 1 to 80 wt. %, from about 5 to 50 wt. %, or from about 10 to 35 wt. % of the one or more organic solvents, based on total weight of the composition. The organic solvent can comprise an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

In addition to the component, the composition can comprise water.

The component of the composition can comprise a corrosion inhibitor in addition to the one or more cationic polymer salts. The composition can comprise from about 0.1 to 20 wt. %, 0.1 to 10 wt. %, or 0.1 to 5 wt. % of the one or more additional corrosion inhibitors, based on total weight of the composition. A composition of the invention can comprise from 0 to 10 percent by weight of the one or more additional corrosion inhibitors, based on total weight of the composition. The composition can comprise 1.0 wt. %, 1.5 wt. %, 2.0 wt. %, 2.5 wt. %, 3.0 wt. %, 3.5 wt. %, 4.0 wt. %, 4.5 wt. %, 5.0 wt. %, 5.5 wt. %, 6.0 wt. %, 6.5 wt. %, 7.0 wt. %, 7.5 wt. %, 8.0 wt. %, 8.5 wt. %, 9.0 wt. %, 9.5 wt. %, 10.0 wt. %, 10.5 wt. %, 11.0 wt. %, 11.5 wt. %, 12.0 wt. %, 12.5 wt. %, 13.0 wt. %, 13.5 wt. %, 14.0 wt. %, 14.5 wt. %, or 15.0 wt. % by weight of the one or more additional corrosion inhibitors, based on total weight of the composition. Each system can have its own requirements, and the weight percent of one or more additional corrosion inhibitors in the composition can vary with the system in which it is used.

The one or more additional corrosion inhibitors can comprise an imidazoline compound, a quaternary ammonium compound, a pyridinium compound, or a combination thereof.

The one or more additional corrosion inhibitor component can comprise an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (1A) or an imidazoline derivative. Representative imidazoline derivatives include an imidazolinium compound of Formula (2A) or a bis-quaternized compound of Formula (3A).

The one or more additional corrosion inhibitor component can include an imidazoline of Formula (1A):

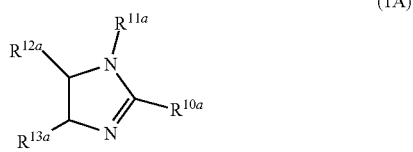

(1A)

wherein $R^{10a}$ is a $C_1$-$C_{20}$ alkyl or a $C_1$-$C_{20}$ alkoxyalkyl group; $R^{11a}$ is hydrogen, $C_1$-$C_6$ alkyl, $C_1$-$C_6$ hydroxyalkyl, or $C_1$-$C_6$ arylalkyl; and $R^{12a}$ and $R^{13a}$ are independently hydrogen or a $C_1$-$C_6$ alkyl group. Preferably, the imidazoline includes an $R^{10a}$ which is the alkyl mixture typical in tall oil fatty acid (TOFA), and $R^{11a}$, $R^{12a}$ and $R^{13a}$ are each hydrogen.

The one or more additional corrosion inhibitor component can include an imidazolinium compound of Formula (2A):

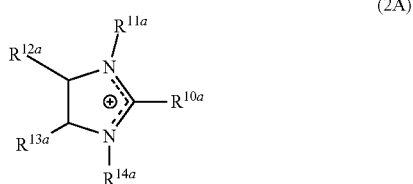

(2A)

wherein $R^{10a}$ is a $C_1$-$C_{20}$ alkyl or a $C_1$-$C_{20}$ alkoxyalkyl group; $R^{11a}$ and $R^{14a}$ are independently hydrogen, $C_1$-$C_6$ alkyl, $C_1$-$C_6$ hydroxyalkyl, or $C_1$-$C_6$ arylalkyl; $R^{12a}$ and $R^{13a}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The one or more additional corrosion inhibitors can comprise a bis-quaternized compound having the formula (3A):

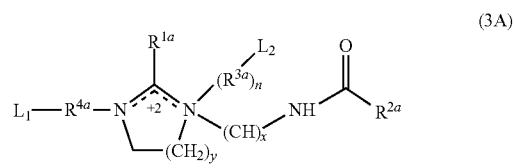

(3A)

wherein:

$R^{1a}$ and $R^{2a}$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof;

$R^{3a}$ and $R^{4a}$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof;

$L_1$ and $L_2$ are each independently absent, H, —COOH, —SO$_3$H, —PO$_3$H$_2$, —COOR$^{5a}$, —CONH$_2$, —CONHR$^{5a}$, or —CON(R$^{5a}$)$_2$;

$R^{5a}$ a is each independently a branched or unbranched alkyl, aryl, alkylaryl, alkylheteroaryl, cycloalkyl, or heteroaryl group having from 1 to about 10 carbon atoms;

n is 0 or 1, and when n is 0, $L_2$ is absent or H;

x is from 1 to about 10; and y is from 1 to about 5. Preferably, $R^{1a}$ and $R^{2a}$ are each independently $C_6$-$C_{22}$ alkyl, $C_8$-$C_{20}$ alkyl, $C_{12}$-$C_{18}$ alkyl, $C_{16}$-$C_{18}$ alkyl, or a combination thereof; $R^{1a}$ and $R^{4a}$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1; $R_3$ and $R_4$ are —C$_2$H$_2$—; $L_1$ is —COOH, —SO$_3$H, or —PO$_3$H$_2$; and $L_2$ is absent, H, —COOH, —SO$_3$H, or —PO$_3$H$_2$. For example, $R^{1a}$ and $R^{2a}$ can be derived from a mixture of tall oil fatty acids and are predominantly a mixture of $C_{17}H_{33}$ and $C_{17}H_{31}$ or can be $C_{16}$-Cis alkyl; $R^{1a}$ and $R^{4a}$ can be $C_2$-$C_3$ alkylene such as —C$_2$H$_2$—; n is 1 and $L_2$ is —COOH or n is 0 and $L_2$ is absent or H; x is 2; y is 1; $R^{3a}$ and $R^{4a}$ are —C$_2$H$_2$—; and $L_1$ is —COOH.

It should be appreciated that the number of carbon atoms specified for each group of formula (3A) refers to the main chain of carbon atoms and does not include carbon atoms that may be contributed by substituents.

The one or more additional corrosion inhibitors can comprise a bis-quaternized imidazoline compound having the formula (3A) wherein $R^{1a}$ and $R^{2a}$ are each independently $C_6$-$C_{22}$ alkyl, $C_8$-$C_{20}$ alkyl, $C_{12}$-$C_{18}$ alkyl, or $C_{16}$-$C_{18}$ alkyl or a combination thereof; $R^{4a}$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —SO$_3$H, or —PO$_3$H$_2$; and $L_2$ is absent or H. Preferably, a bis-quaternized compound has the formula (3A) wherein $R^{1a}$ and $R^{2a}$ are each independently $C_{16}$-$C_{18}$ alkyl; $R^{4a}$ is —$C_2H_2$—; x is 2; y is 1; n is 0; $L_1$ is —COOH, —SO$_3$H, or —PO$_3$H$_2$ and $L_2$ is absent or H.

The one or more additional corrosion inhibitors can be a quaternary ammonium compound of Formula (4A):

(4A)

wherein $R^{1a}$, $R^{2a}$, and $R^{3a}$ are independently $C_1$ to $C_{20}$ alkyl, $R^{4a}$ is methyl or benzyl, and $X^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula [N$^+$R$^{5a}$R$^{6a}$R$^{7a}$R$^{8a}$][X$^-$] wherein $R^{5a}$, $R^{6a}$, $R^{7a}$, and $R^{8a}$ contain one to 18 carbon atoms, and X is Cl, Br or I. For the quaternary salts, $R^{5a}$, $R^{6a}$, $R^{7a}$, and $R^{8a}$ can each be independently alkyl (e.g., $C_1$-Cis alkyl), hydroxyalkyl (e.g., $C_1$-Cis hydroxyalkyl), and arylalkyl (e.g., benzyl). The mono or polycyclic aromatic amine salt with an alkyl or alkylaryl halide include salts of the formula [N$^+$R$^{5a}$R$^{6a}$R$^{7a}$R$^{8a}$][X$^-$] wherein $R^{5a}$, $R^{6a}$, $R^{7a}$, and $R^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The one or more additional corrosion inhibitor component can comprise a pyridinium salt such as those represented by Formula (5A):

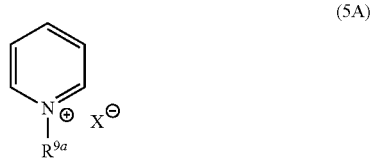

(5A)

wherein $R^{9a}$ is an alkyl group, an aryl group, or an arylalkyl group, wherein said alkyl groups have from 1 to about 18 carbon atoms and X$^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The one or more additional corrosion inhibitor components can include additional corrosion inhibitors such as phosphate esters, monomeric or oligomeric fatty acids, or alkoxylated amines.

The one or more additional corrosion inhibitor component can comprise a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a more broad distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The one or more additional corrosion inhibitor component can include a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The one or more additional corrosion inhibitor component can comprise an alkoxylated amine. The alkoxylated amine can be an ethoxylated alkyl amine. The alkoxylated amine can be ethoxylated tallow amine.

The component of the composition can comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. Such compounds are used as synergists in the composition. The organic sulfur compound can constitute 0.5 to 15 wt. % of the composition, based on total weight of the composition, preferably about 1 to about 10 wt. % and more preferably about 1 to about 5 wt. %. The organic sulfur compound can constitute 1, 2, 3, 4, 5, 6, 7, 8, 9, 10, 11, 12, 13, 14 or 15 wt. % of the composition.

The component of the composition can further include a demulsifier. Preferably, the demulsifier comprises an oxyalkylate polymer, such as a polyalkylene glycol. The demulsifier can constitute from about 0.1 to 10 wt. %, from about 0.5 to 5 wt. %, or from about 0.5 to 4 wt. of the composition, based on total weight of the composition. The demulsifier can constitute 0.5, 1, 1.5, 2, 2.5, 3, 3.5, 4, 4.5 or 5 wt. % of the composition.

The component of the composition can include an asphaltene inhibitor. The composition can comprise from about 0.1 to 10 wt. %, from about 0.1 to 5 wt. %, or from about 0.5 to 4 wt. % of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The component of the composition can include a paraffin inhibitor. The composition can comprise from about 0.1 to 10 wt. %, from about 0.1 to 5 wt. %, or from about 0.5 to 4 wt. % of a paraffin inhibitor, based on total weight of the composition. Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The component of the composition can include a scale inhibitor. The composition can comprise from about 0.1 to 20 wt. %, from about 0.5 to 10 wt. %, or from about 1 to 10 wt. % of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The component of the composition can include an emulsifier. The composition can comprise from about 0.1 to 10 wt. %, from about 0.5 to 5 wt. %, or from about 0.5 to 4 wt. % of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkylsaccharide emulsifiers).

The component of the composition can include a water clarifier. The composition can comprise from about 0.1 to 10 wt. %, from about 0.5 to 5 wt. %, or from about 0.5 to 4 wt. % of a water clarifier, based on total weight of the composition. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The component of the composition can include a dispersant. The composition can comprise from about 0.1 to 10 wt. %, from about 0.5 to 5 wt. %, or from about 0.5 to 4 wt. % of a dispersant, based on total weight of the composition. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The component of the composition can include an emulsion breaker. The composition can comprise from about 0.1 to 10 wt. %, from about 0.5 to 5 wt. %, or from about 0.5 to 4 wt. % of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and nonionic surfactants, and resins, such as phenolic and epoxide resins.

The component of the composition can include a hydrogen sulfide scavenger. The composition can comprise from about 1 to 50 wt. %, from about 1 to 40 wt. %, or from about 1 to 30 wt. % of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The component of the composition can include a gas hydrate inhibitor. The composition can comprise from about 0.1 to 25 wt. %, from about 0.5 to 20 wt. %, or from about 1 to 10 wt. % of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The component of the composition can include a kinetic hydrate inhibitor. The composition can comprise from about 0.1 to 25 wt. %, from about 0.5 to 20 wt. %, or from about 1 to 10 wt. % of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The component of the composition can include a biocide. The composition can comprise from about 0.1 to 10 wt. %, from about 0.5 to 5 wt. %, or from about 0.5 to 4 wt. % of a biocide, based on total weight of the composition. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DB-NPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

The component of the composition can include a pH modifier. The composition can comprise from about 0.1 to 20 wt. %, from about 0.5 to 10 wt. %, or from about 0.5 to 5 wt. % of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The component of the composition can include a surfactant. The composition can comprise from about 0.1 to 10 wt. %, from about 0.5 to 5 wt. %, or from about 0.5 to 4 wt. % of a surfactant, based on total weight of the composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

Corrosion inhibitor compositions made according to the invention can further include additional functional agents or additives that provide a beneficial property. For example, additional agents or additives can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (i.e., dyes, odorants, perfumes), or other additives suitable for formulation with a corrosion inhibitor composition, and mixtures thereof. Additional agents or additives will vary according to the particular corrosion inhibitor composition being manufactured and its intend use as one skilled in the art will appreciate.

Alternatively, the compositions can not contain any of the additional agents or additives.

Additionally, the corrosion inhibitors of the invention can be formulated into compositions comprising the following components. These formulations include the ranges of the components listed and can optionally include additional agents. The values in the Tables below are weight percents.

| | Component | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Cationic polymer salt | 0.1-20 | 0.1-20 | 0.1-20 | 0.1-20 | 0.1-20 | 0.1-20 | 10-20 | 10-20 | 10-20 | 10-20 | 10-20 | 0.1-20 |
| Organic solvent | 5-40 | — | 5-50 | — | 5-50 | 5-50 | 5-40 | — | 5-50 | — | — | 10-20 |
| Additional corrosion inhibitor | 0.1-20 | 0.1-20 | — | — | — | — | 0.1-20 | 0.1-20 | — | — | — | 0.1-20 |
| Asphaltene inhibitor | 0.1-5 | 0.1-5 | 0.1-5 | 0.1-5 | — | — | 0.1-5 | 0.1-5 | 0.1-5 | — | — | 0.1-5 |
| Scale inhibitor | 1-10 | 1-10 | 1-10 | 1-10 | 1-10 | — | 1-10 | 1-10 | 1-10 | 1-10 | — | 1-10 |
| Gas hydrate inhibitor | — | — | — | — | — | — | — | — | — | — | — | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | |
| Water | 0.00 | 0-40 | 0-10 | 0-60 | 0-15 | 0-25 | 0.00 | 0-40 | 0-10 | 0-65 | 0-75 | |

| | Component | | | | | | | | | | | |
|---|---|---|---|---|---|---|---|---|---|---|---|---|
| | 13 | 14 | 15 | 16 | 17 | 18 | 19 | 20 | 21 | 22 | 23 | 24 |
| Cationic polymer salt | 0.1-20 | 0.1-20 | 0.1-20 | 0.1-20 | 0.1-20 | 0.1-20 | 10-20 | 10-20 | 10-20 | 10-20 | 10-20 | 10-20 |
| Organic solvent | — | 10-20 | — | 10-35 | 10-35 | — | 10-15 | — | — | 10-35 | 10-35 | — |
| Additional corrosion inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Asphaltene inhibitor | 0.1-5 | — | — | — | — | — | 0.1-5 | — | — | — | — | — |
| Scale inhibitor | 1-10 | 1-10 | — | — | 1-10 | — | 1-10 | 1-10 | — | — | — | 1-10 |

-continued

| | Component | | | | | | | | | | | |
|---|---|---|---|---|---|---|---|---|---|---|---|---|
| | 13 | 14 | 15 | 16 | 17 | 18 | 19 | 20 | 21 | 22 | 23 | 24 |
| Gas hydrate inhibitor | 0.1-25 | 0.1-25 | 0.1-25 | — | — | — | 0.1-25 | 0.1-25 | 0.1-25 | — | 0.1-25 | — |
| Biocide | — | — | — | — | — | 0.5-5 | 0.5-5 | 0.5-5 | 0.5-5 | 0.5-5 | — | — |
| Water | 0-20 | 0-5 | 0-35 | 0-25 | 0-15 | 0-55 | 0.00 | 0-20 | 0-30 | 0-20 | 0.00 | 0-50 |

Another aspect of the invention is a method of inhibiting corrosion at a surface. The method comprises either: contacting the surface with a cationic polymer salt to inhibit corrosion on the surface; contacting the surface with a composition comprising the cationic polymer salt and a component comprising an organic solvent, a corrosion inhibitor, an organic sulfur compound, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof to inhibit corrosion on the surface; or adding the compound or the composition to a fluid which contacts the surface to inhibit corrosion on the surface. The cationic polymer salt can be one or more of the cationic polymer salts as described herein such as compounds 1-15. The composition can be any composition as described herein.

The polymer salts/compositions can be used for inhibiting corrosion in oil and gas applications such as by treating a gas or liquid stream with an effective amount of a compound or composition as described herein. The compounds and compositions can be used in any industry where it is desirable to inhibit corrosion at a surface.

The polymer salts/compositions can be used in water systems, condensate/oil systems/gas systems, or any combination thereof. For example, the polymer salts/compositions can be used in controlling scale on heat exchanger surfaces.

The polymer salts/compositions can be applied to a gas or liquid produced, or used in the production, transportation, storage, and/or separation of crude oil or natural gas.

The polymer salts/compositions can be applied to a gas stream used or produced in a coal-fired process, such as a coal-fired power plant.

The polymer salts/compositions can be applied to a gas or liquid produced or used in a waste-water process, a farm, a slaughter house, a land-fill, a municipality waste-water plant, a coking coal process, or a biofuel process.

A fluid to which the polymer salts/compositions can be introduced can be an aqueous medium. The aqueous medium can comprise water, gas, and optionally liquid hydrocarbon.

A fluid to which the polymer salts/compositions can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene.

The fluid or gas can be a refined hydrocarbon product.

A fluid or gas treated with a polymer salt/composition can be at any selected temperature, such as ambient temperature or an elevated temperature. The fluid (e.g., liquid hydrocarbon) or gas can be at a temperature of from about 40° C. to about 250° C. The fluid or gas can be at a temperature of from −50° C. to 300° C., 0° C. to 200° C., 10° C. to 100° C., or 20° C. to 90° C. The fluid or gas can be at a temperature of 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. The fluid or gas can be at a temperature of 85° C., 86° C., 87° C., 88° C., 89° C., 90° C., 91° C., 92° C., 93° C., 94° C., 95° C., 96° C., 97° C., 98° C., 99° C., or 100° C.

The polymer salts/compositions can be added to a fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The fluid or gas in which the polymer salts/compositions are introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units.

The polymer salts/compositions can be introduced into a fluid or gas by any appropriate method for ensuring dispersal through the fluid or gas.

The polymer salts/compositions can be added to the hydrocarbon fluid before the hydrocarbon fluid contacts the surface.

The polymer salts/compositions can be added at a point in a flow line upstream from the point at which corrosion prevention and/or schmoo removal is desired.

The polymer salts/compositions can be injected using mechanical equipment such as chemical injection pumps, piping tees, injection fittings, atomizers, quills, and the like.

The polymer salts/compositions of the invention can be introduced with or without one or more additional polar or non-polar solvents depending upon the application and requirements.

The polymer salts/compositions can be pumped into an oil and/or gas pipeline using an umbilical line. A capillary injection system can be used to deliver the polymer salts/compositions to a selected fluid.

A fluid to which the compositions can be introduced can be an aqueous medium. The aqueous medium can comprise water, gas, and optionally liquid hydrocarbon. A fluid to which the polymer salts/compositions can be introduced can be a liquid hydrocarbon.

The polymer salts/compositions can be introduced into a liquid and mixed.

The polymer salts/compositions can be injected into a gas stream as an aqueous or non-aqueous solution, mixture, or slurry.

The fluid or gas can be passed through an absorption tower comprising polymer salts/compositions.

The polymer salts/compositions can be applied to a fluid or gas to provide any selected concentration. In practice, the polymer salts/compositions are typically added to a flow line to provide an effective treating dose of the described compounds from about 0.01 to about 5,000 ppm. The polymer salts/compositions can be applied to a fluid or gas to provide an actives concentration of about 1 parts per million (ppm) to about 1,000,000 ppm, about 1 parts per million (ppm) to about 100,000 ppm, or about 10 ppm to about 75,000 ppm. The polymer salts/compositions can be applied to a fluid to provide an actives concentration of about 100 ppm to about 10,000 ppm, about 200 ppm to about 8,000 ppm, or about 500 ppm to about 6,000 ppm. The actives concentration means the concentration of the compounds of formula (1).

The polymer salts/compositions can be applied to a fluid or gas to provide actives concentration of 0.1 ppm, 0.5 ppm, 1 ppm, 2 ppm, 5 ppm, 10 ppm, 20 ppm, 100 ppm, 200 ppm, 500 ppm, or 1,000 ppm. The polymer salts/compositions can be applied to a fluid or gas to provide an actives concentration of 0.125 ppm, 0.25 ppm, 0.625 ppm, 1 ppm, 1.25 ppm, 2.5 ppm, 5 ppm, 10 ppm, or 20 ppm. Each system can have its own dose level requirements, and the effective dose level of polymer salts/compositions to sufficiently reduce the rate of corrosion can vary with the system in which it is used.

The polymer salts/compositions can be applied continuously, in batch, or a combination thereof. The polymer salts/compositions doses can be continuous to prevent corrosion. The polymer salts/compositions doses can be intermittent (i.e., batch treatment) or the polymer salts/compositions doses can be continuous/maintained and/or intermittent to inhibit corrosion.

Dosage rates for continuous treatments typically range from about 10 to about 500 ppm, or about 10 to about 200 ppm. Dosage rates for batch treatments typically range from about 10 to about 400,000 ppm, or about 10 to about 20,000 ppm. The polymer salts/compositions can be applied as a pill to a pipeline, providing a high dose (e.g., 20,000 ppm) of the composition.

The flow rate of a flow line in which the polymer salt/composition is used can be between 0 and 100 feet per second, or between 0.1 and 50 feet per second. The polymer salts/compositions can also be formulated with water in order to facilitate addition to the flow line.

The surface can be a part of a wellbore or equipment used in the production, transportation, storage, and/or separation of a fluid such as crude oil or natural gas.

More specifically, the surface can be a part of equipment used a coal-fired process, a waste-water process, a farm, a slaughter house, a land-fill, a municipality waste-water plant, a coking coal process, or a biofuel process. Preferably, the surface can be a part of equipment used in the production of crude oil or natural gas.

The equipment can comprise a pipeline, a storage vessel, downhole injection tubing, a flow line, or an injection line.

The polymer salts/compositions of the invention can be used for inhibiting corrosion in other applications.

The polymer salts/compositions are useful for corrosion inhibition of containers, processing facilities, or equipment in the food service or food processing industries. The polymer salts/compositions have particular value for use on food packaging materials and equipment, and especially for cold or hot aseptic packaging. Examples of process facilities in which the polymer salts/compositions can be employed include a milk line dairy, a continuous brewing system, food processing lines such as pumpable food systems and beverage lines, ware wash machines, low temperature ware wash machines, dishware, bottle washers, bottle chillers, warmers, third sink washers, processing equipment such as tanks, vats, lines, pumps and hoses (e.g., dairy processing equipment for processing milk, cheese, ice cream and other dairy products), and transportation vehicles. The polymer salts/compositions can be used to inhibit corrosion in tanks, lines, pumps, and other equipment used for the manufacture and storage of soft drink materials, and also used in the bottling or containers for the beverages.

The polymer salts/compositions can also be used on or in other industrial equipment and in other industrial process streams such as heaters, cooling towers, boilers, retort waters, rinse waters, aseptic packaging wash waters, and the like. The polymer salts/compositions can be used to treat surfaces in recreational waters such as in pools, spas, recreational flumes and water slides, fountains, and the like.

The polymer salts/compositions can be used to inhibit the corrosion of metal surfaces contacted with cleaners in surfaces found in janitorial and/or housekeeping applications, food processing equipment and/or plant applications, and in laundry applications. For example, the corrosion of washers, such as tunnel washers for washing textiles, can be inhibited according to methods disclosed herein.

The polymer salts/compositions can be used or applied in combination with low temperature dish and/or warewash sanitizing final rinse, toilet bowl cleaners, and laundry bleaches. The compounds, compositions and methods can be used to treat metal surfaces, such as ware, cleaned and/or sanitized with corrosive sources.

The compounds, compositions and methods disclosed herein protect surfaces from corrosion caused by hypochlorite bleach. A method can include providing the corrosion inhibitor polymer salts/compositions to a surface treated with a hypochlorite solution in order to inhibit corrosion caused by the hypochlorite solution. The method can include preparing an aqueous use composition of the present corrosion inhibitor composition. The method can further include contacting a surface, such as a hard metal surface, in need of corrosion inhibition due to contact with a hypochlorite solution.

The polymer salts/compositions can be dispensed in any suitable method generally known by one skilled in the art. For example, a spray-type dispenser can be used, such as that disclosed in U.S. Pat. Nos. 4,826,661, 4,690,305, 4,687,121, 4,426,362 and in U.S. Pat. Nos. Re 32,763 and 32,818, the disclosures of which are incorporated by reference herein. A spray-type dispenser functions by impinging a water spray upon an exposed surface of a composition to dissolve a portion of the composition, and then immediately directing the concentrate solution including the composition out of the dispenser to a storage reservoir or directly to a point of use.

The polymer salts/compositions can be dispensed by immersing either intermittently or continuously in water. The composition can then dissolve, for example, at a controlled or predetermined rate. The rate can be effective to maintain a concentration of dissolved agent that is effective for use according to the methods disclosed herein.

EXAMPLES

The following non-limiting examples are provided to further illustrate various aspects of the present disclosure. All chemicals were used as received from the supplier unless otherwise noted.

NMR samples of the cationic polymer salts were prepared in D$_2$O. All spectra were acquired at 25° C. Quantitative proton ($^1$H) and carbon ($^{13}$C) were acquired using a single-pulse sequence implemented on an AGILENT 500 MHz spectrometer equipped with a 10 mm broad-band probe for carbon or a 5 mm two-channel probe for proton with Z-gradient. $^1$H spectra were acquired with 4-8 scans. $^{13}$C spectra were acquired with 400-500 scans. Data were processed and analyzed using MestReNova v. 9 (Mestrelab, Spain).

The chemical shifts (ppm) are reported relative to TMS (tetramethylsilane) using the residual solvent peak as reference unless otherwise noted. The following abbreviations are used to express the multiplicities: s=singlet; d=doublet; t=triplet; q=quartet; m=multiplet; br=broad.

Mass spectroscopy of the cationic surfactants was conducted on a Q EXACTIVE ORBITRAP high resolution mass spectrometer (Thermo Fisher Scientific) equipped with a quadrupole as an ion filter and with an electrospray ionization (ESI) source. Surfactant samples were diluted to about 100 ppm and then injected into the mass spectrometer by infusion at the flow rate of 10 μL/minute. Spectra were acquired in positive ESI mode; scan range: 50-750 m/z; resolution: 140 k; AGC target: 3$^6$; sheath gas flow rate: 2 (arbitrary unit); auxiliary gas flow rate: 0 (arbitrary unit); spray voltage: 2.5 kV; capillary temperature: 150° C.; auxiliary gas heater temperature: 30° C.; and S-Len RF level: 50. Data were acquired and analyzed by XCALIBUR and FREESTYLE software (Thermo Fisher Scientific).

Example 1: Synthesis of Multiple Quaternary Cationic Surfactants with Methyl Groups Diethylenetriamine (DETA, 10.32 grams, 0.10 mol) and 3-chloro-2-hydroxypropyl trimethylammonium chloride (156.7 grams, 60.0%, 0.50 mol, (Sigma-Aldrich) were added to a 500 mL four-neck round bottom flask equipped with a mechanical stirrer, a thermometer, a temperature controller, a condenser, and an addition funnel. The reaction mixture was stirred and gently heated to 60° C. The pH value of the reaction was continuously monitored. Sodium hydroxide (50% aqueous solution) was slowly added to the reaction flask and the temperature was held constant at 60° C. The pH value of reaction solution was measured and was held constant above 7.5. The reaction temperature was raised to 85° C. and held constant for 5 hours. The reaction scheme is as follows wherein R$_1$, R$_2$ and R$_3$ are methyl and n is 1:

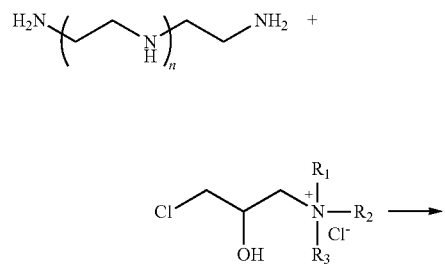

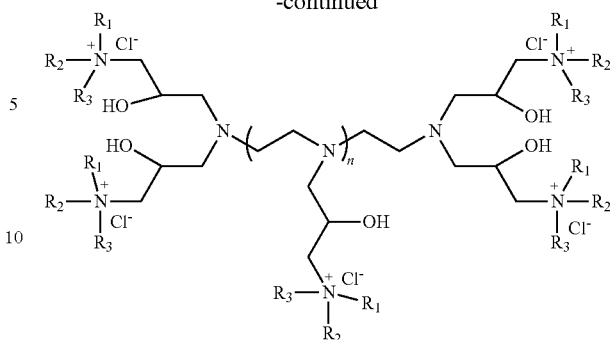

$^{13}$C NMR (500 MHz, D$_2$O, 25° C.) spectra showed the chemical shifts at 44-46 ppm and 58-59.3 ppm which were assigned to the reacted DETA. The resonance signal at 47.5 ppm represents the chlorinated methylene in unreacted 3-chloro-2-hydroxypropyl trimethylammonium chloride. The total amount of 3-chloro-2-hydroxypropyl trimethylammonium chloride was determined based on the sharp signal at 54.5 ppm from the methyl groups. The average charge per DETA was 4.8, consistent with theoretical values of 5 charges. MS (ESI): calc. [M-2Cl$^-$]$^{2+}$ 394.275, found 394.278; calc. [M-3Cl$^-$]$^{3+}$ 251.193, found 251.195; calc. [M-4Cl$^-$]$^{4+}$ 179.655, found 179.654; calc. [M-5Cl$^-$]$^{5+}$ 136.73, found 136.73.

Example 2: Synthesis of Multiple Quaternary Cationic Surfactants with Lauryl Groups Multiple quaternary cationic surfactants with lauryl chains were synthesized by reacting diethylenetriamine (DETA) and 3-chloro-2-hydroxypropyl-dodecyl-dimethyl-ammonium chloride (QUAB 342™ from Quab Chemicals, Saddle Brook, N.J.). Diethylenetriamine (5.16 grams, 0.05 mol) and 3-chloro-2-hydroxypropyl-dodecyl-dimethylammonium chloride (222.66 grams, 38.4 wt. %, 0.25 mol) were charged to a 500 mL four-neck round bottom flask equipped with a mechanical stirrer, a thermometer, a temperature controller, a condenser, and an addition funnel. The reaction mixture was stirred and gently heated to 60° C. The pH value of the reaction was continuously monitored. Sodium hydroxide (50% aqueous solution) was slowly added to the reaction flask and the temperature was held constant at 60° C. The pH value of reaction solution was measured and was held constant above 7.5. The reaction temperature was raised to 85° C. and held constant for 5 hours.

The mass spectroscopy data showed that the reaction product contained a mixture of 2 quaternary-2 dimethyl dodecyl ammonium chlorides (MS (ESI): calc. [M-2Cl$^-$]$^{2+}$ 321.83, found 321.83); 3 quaternary-3 dimethyl dodecyl ammonium chlorides (MS (ESI): calc. [M-Cl$^-$]$^+$ 983.89, found 983.89; calc. [M-2Cl$^-$]$^{2+}$ 474.46, found 474.46; 4 quaternary-4 dimethyl dodecyl ammonium chlorides (MS (ESI): calc. [M-Cl$^-$]$^+$ 1289.14, found 1289.13, calc. [M-2Cl$^-$]$^{2+}$ 627.08, found 627.08; calc. [M-3Cl$^-$]$^{3+}$ 406.40, found 406.40; calc. [M-4Cl$^-$]$^{4+}$ 296.06, found 296.06); and 5 quaternary-5 dimethyl dodecyl ammonium chlorides (MS (ESI): calc. [M-2Cl$^-$]$^{2+}$ 779.71, found 779.71; calc. [M-3Cl$^-$]$^{3+}$ 508.15, found 508.48; calc. [M-4Cl$^-$]$^{4+}$ 372.37, found 372.37). Surface tension, 63.63 mN/m @0.050 wt % aqueous solution.

Example 3: Synthesis of Multiple Quaternary Cationic Surfactants with Different Alkyl Chains A five-quaternary cationic surfactant was synthesized by reacting diethylene triamine (DETA, 10.32 grams, 0.10 mol)

and 3-chloro-2-hydroxypropyl trimethylammonium chloride (62.7 grams, 60.0% 0.20 0 mol) and 3-chloro-2-hydroxypropyl-dimethyldodecylammonium chloride (267.2 grams, 38.4 wt. %, 0.30 mol) (QUAB 342™) using the procedure described in Example 1.

Alternatively, the synthesis can be conducted using a mixture of 3-chloro-2-hydroxypropyl trimethylammonium chloride and 3-chloro-2-hydroxypropyl-dimethyloctadecylammonium chloride with different molar ratios; however a total of 5 moles of trialkylammonium chloride was held constant.

A six-quaternary cationic surfactant was synthesized by reacting triethylene tetraamine (TETA, 12.2 grams, 60 wt. %, 0.05 moles) and 3-chloro-2-hydroxypropyldimethyloctadecylammonium chloride (336.3 grams, 38.0%, 0.30 mol; QUAB 426™ from Quab Chemicals, Saddle Brook, N.J.) in propylene glycol (PP425, 69.9 grams) using the procedure described in Example 1.

It was determined that varying the solvents between a mixture of water/propanediol and water/propanediol/PP425 or water/hexylene glycol achieved a homogenous phase during the reaction. Further, it was found that propanediol and propylene glycol increased the water solubility of multiple cationic surfactants with long alkyl chains.

Compound 1 was synthesized using diethylenetriamine (1 mol), (3-chloro-2-hydroxypropyl) lauryl dimethylammonium chloride (4 mol), and (3-chloro-2-hydroxypropyl) trimethylammonium chloride (1 mol). Mass spectrometry confirmed synthesis of Compound 1: calc. $[M-2Cl^-]^{2+}$ 702.62, found 703.62; calc. $[M-3Cl^-]^{3+}$ 456.76, found 457.09.

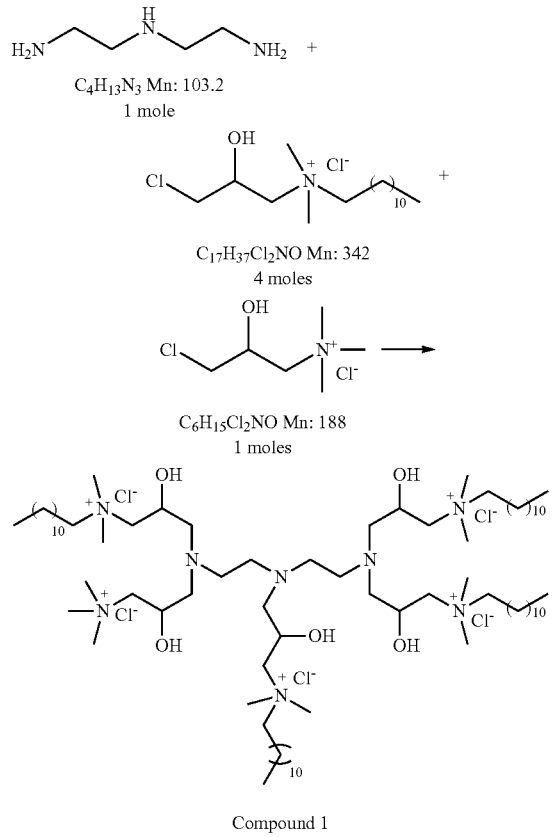

Compound 1

5 HCl

Compound 2 was synthesized using diethylenetriamine (1 mol), (3-chloro-2-hydroxypropyl) lauryl dimethylammonium chloride (3 mol), and (3-chloro-2-hydroxypropyl) trimethylammonium chloride (2 mol). Mass spectrometry confirmed synthesis of Compound 2: calc. $[M-2Cl^-]^{2+}$ 625.54, found 626.53; calc. $[M-3Cl^-]^{3+}$ 405.37, found 405.7; calc. $[M-4Cl^-]^{4+}$ 295.28, found 295.28.

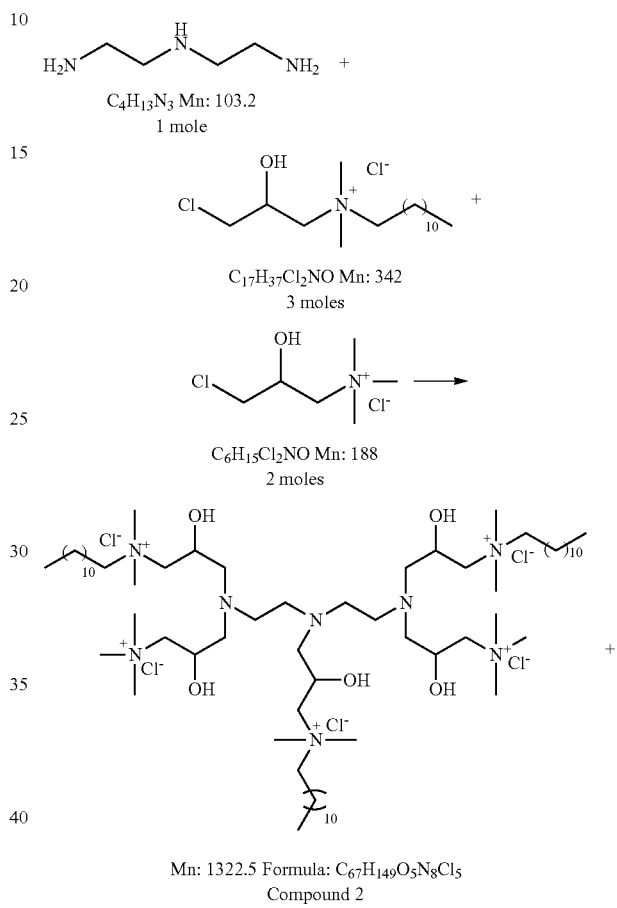

Compound 2

5 HCl

Compound 3 was synthesized using diethylenetriamine (1 mol) and (3-chloro-2-hydroxypropyl) lauryl dimethylammonium chloride (5 mol). Mass spectrometry confirmed synthesis of Compound 3: calc. $[M-2Cl^-]^{2+}$ 779.71, found 779.71; calc. $[M-3Cl^-]^{3+}$ 508.15, found 508.48; calc. $[M-4Cl^-]^{4+}$ 372.37, found 372.37.

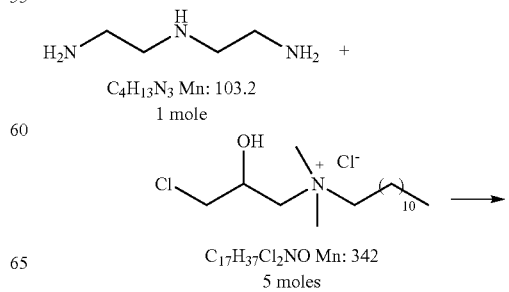

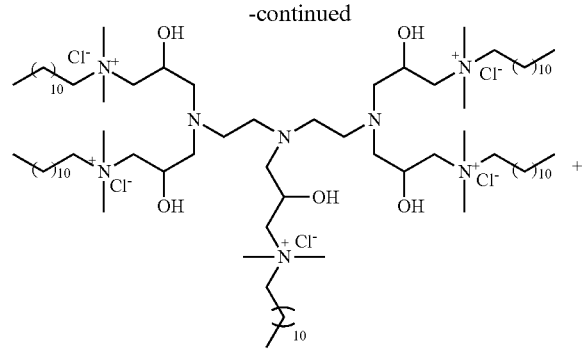

Compound 3

5 HCl

Compound 4 was synthesized using diethylenetriamine (1 mol), (3-chloro-2-hydroxypropyl) octadecyl dimethylammonium chloride (3 mol), and (3-chloro-2-hydroxypropyl) trimethylammonium chloride (2 mol).

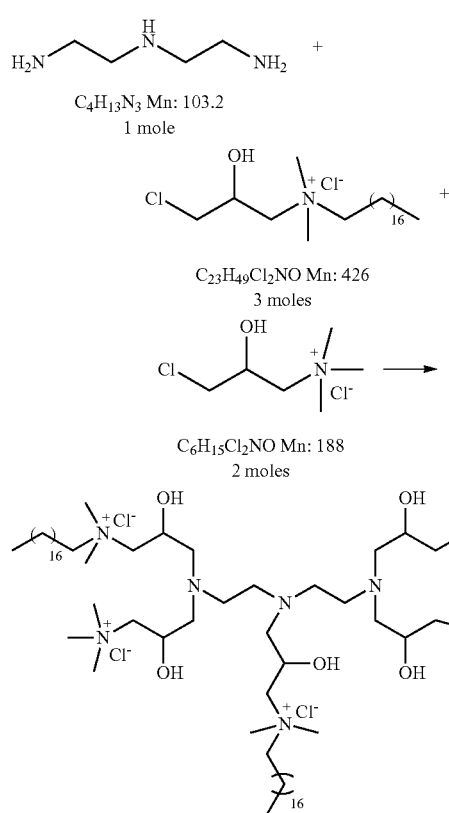

Compound 4

5 HCl

Compound 5 and 6 were synthesized similarly to Compounds 1-3, as described above. Mass spectrometry confirmed synthesis of Compound 5: calc. $[M-2Cl^-]^{2+}$ 548.45, found 549.45; calc. $[M-3Cl^-]^{3+}$ 353.98, found 354.64; calc. $[M-4Cl^-]^{4+}$ 256.74, found 256.74. Mass spectrometry confirmed synthesis of Compound 6: $[M-5Cl^-]^{5+}$ 167.56, found 167.56.

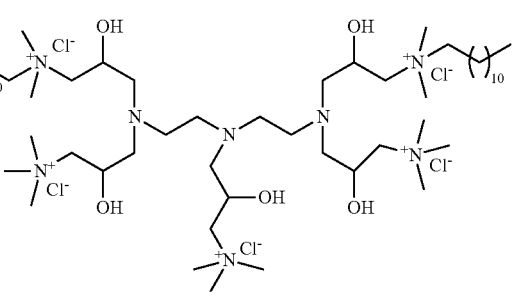

Compound 5

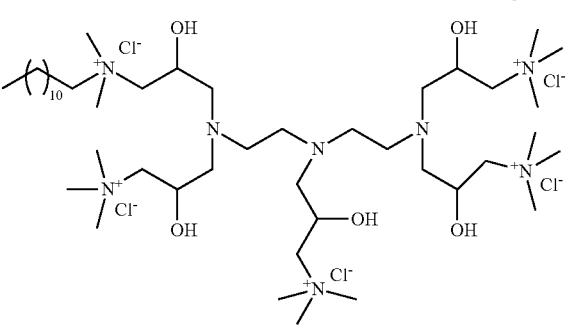

Compound 6

Compounds 7-12 were synthesized in a similar manner as compound 4 described above. Different ratios of reactants yielded different proportions of long chain alkyl groups in the cationic polymer.

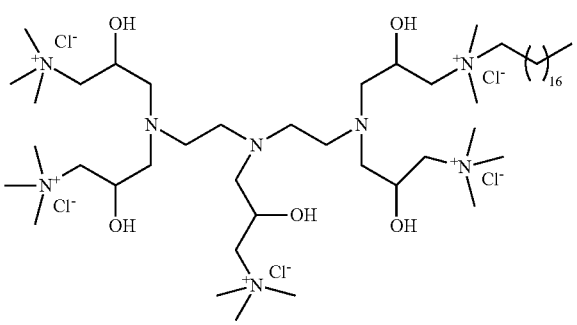

Compound 7

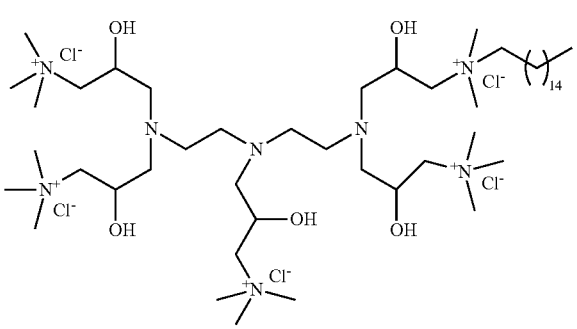

Compound 8

-continued

Compound 9

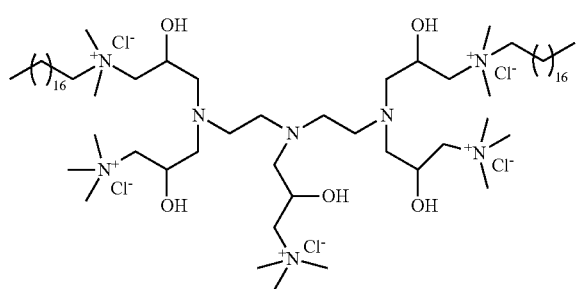

Compound 10

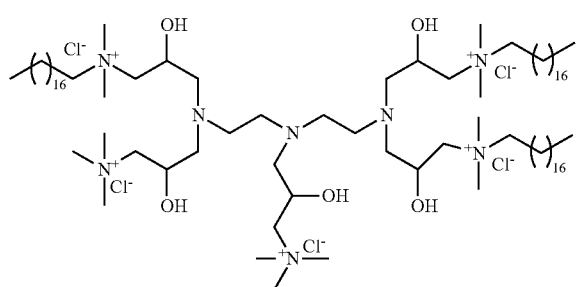

Compound 11

Compound 12

-continued

Compound 13

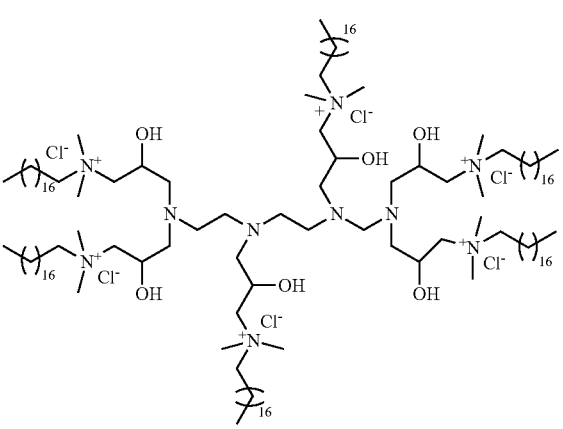

Various multiple cationic surfactants were synthesized using the above-mentioned synthetic scheme, e.g. DETA, TETA, 3-chloro-2-hydroxypropyl trimethylammonium chloride (QUAT 188™ cationic monomer from Dow Chemical Company of Midland, Mich.) and QUAB 426™ reactants, and the products are summarized in Table 1, below. Regarding the structures reported in Table 1, "5Q-1 Stearyl (C18)/4 trimethyl quats" means that the product has 5 total quaternary groups (5Q) of which 1 quat group had $R_1$ and $R_2$ as methyl and $R_3$ as stearyl, and 4 quat groups had $R_1$, $R_2$ and $R_3$ as methyl, and n=1. Likewise, "5Q-2 Stearyl (C18)/3 trimethyl quats" means that the product has 5 total quaternary groups (5Q) of which 2 quat groups had $R_1$ and $R_2$ as methyl and $R_3$ as stearyl, and 3 quat groups had $R_1$, $R_2$ and $R_3$ as methyl, and n=1. "5Q-3 Stearyl (C18)/2 trimethyl quats" means that the product has 5 total quaternary groups (5Q) of which 3 quat groups had $R_1$ and $R_2$ as methyl and $R_3$ as stearyl, and 2 quat groups had $R_1$, $R_2$ and $R_3$ as methyl, and n=1. "5Q-4 Stearyl ($C_{18}$)/1 trimethyl quat" means that the product has 5 total quaternary groups (5Q) of which 4 quat groups had $R_1$ and $R_2$ as methyl and $R_3$ as stearyl, and 1 quat group had $R_1$, $R_2$ and $R_3$ as methyl, and n=1. "5Q-5 Stearyl (C18)" means that the product has 5 total quaternary groups (5Q) of which 5 quat groups had $R_1$ and $R_2$ as methyl and $R_3$ as stearyl, and n=1. "6Q-6 Stearyl(C18)" means that the product has 6 total quaternary groups (6Q) of which 6 quat groups had $R_1$ and $R_2$ as methyl and $R_3$ as stearyl, and n=2.

TABLE 1

Physical properties of multiple quaternary cationic surfactants

| Compound | | | | | Active, wt % | |
| --- | --- | --- | --- | --- | --- | --- |
| No. | Structure | Polyamine | Ratio of QUAB426/QUAT188 | Solvent | Calculated, % | Measured, % |
| 7 | 5Q-1 Stearyl (C18)/4 trimethyl quats | DETA | 1/4 | Water/ Propanediol | 51.47 | 52.58 |
| 9 | 5Q-2 Stearyl | DETA | 2/3 | Water/ Propanediol | 46.54 | 51.3 |

TABLE 1-continued

Physical properties of multiple quaternary cationic surfactants

| Compound No. | Structure | Polyamine | Ratio of QUAB426/QUAT188 | Solvent | Active, wt % Calculated, % | Measured, % |
|---|---|---|---|---|---|---|
| 10 | (C18)/3 trimethyl quats 5Q-3 Stearyl (C18)/2 trimethyl quats | DETA | 3/2 | Water/ Propanediol | 43.41 | 61.77 |
| 11 | 5Q-4 Stearyl (C18)/1 trimethyl quat | DETA | 4/1 | Water/ Propanediol/ PP425 | 33.68 | 62.88 |
| 12 | 5Q-5 Stearyl (C18) | DETA | 5/0 | Water/ Propanediol/ PP425 | 33.74 | 53.99 |
| 13 | 6Q-6 Stearyl (C18) | TETA | 6/0 | Water/ Propanediol/ PP425 | 33.28 | 49.40 |

The mass spectra of Compound 9 showed that the reaction product contained a mixture of 2-C18/3-Trimethyl (MS (ESI): calc. $[M-2Cl^-]^{2+}$ 632.545; found 632.5423; calc. $[M-3Cl^-]^{3+}$410.04, found 410.038; calc. $[M-4Cl^-]^{4+}$ 298.7875, found 298.786; calc. $[M-5Cl^-]^{5+}$232.036, found 232.210); 2-C16/3-Trimethyl (MS (ESI): calc. $[M-2Cl^-]^{2+}$ 604.51; found 604.51 calc. $[M-3Cl^-]^{3+}$391.35, found 391.35; calc. $[M-4Cl^-]^{4+}$284.77, found 284.77; calc. $[M-5Cl^-]^{5+}$220.824, found 220.555); 1-C18/1-C16/3-Trimethyl (MS (ESI): calc. $[M-2Cl^-]^{2+}$ 618.525; found 618.5266; calc. $[M-3Cl^-]^{3+}$400.697, found 400.694; calc. $[M-4Cl^-]^{4+}$ 291.78, found 291.778; calc. $[M-5Cl^-]^{5+}$226.43, found 226.429); 1-C18/4-Trimethyl (MS (ESI): calc. $[M-2Cl^-]^{2+}$ 513.41; found 513.4098; calc. $[M-3Cl^-]^{3+}$330.62, found 330.6166; calc. $[M-4Cl^-]^{4+}$ 239.22, found 239.2202; calc. $[M-5Cl^-]^{5+}$184.38, found 184.3823); and 1-C16/4-Trimethyl (MS (ESI): calc. $[M-2Cl^-]^{2+}$ 449.395; found 449.4368; calc. $[M-3Cl^-]^{3+}$321.27, found 321.2728; calc. $[M-4Cl^-]^{4+}$ 232.21, found 232.212; calc. $[M-5Cl^-]^{5+}$178.776, found 178.776).

Example 4: Surface Tension Measurements and Critical Micelle Concentrations (CMC) Calculations Surface tension measurements were conducted on a Tracker tensiometer (Teclis Instruments) at room temperature. Various concentrations of surfactant solutions were prepared and measurements were conducted.

The surface tension as a function of concentration of the cationic surfactant samples were measured and are listed in Table 2, where NT means not tested.

TABLE 2

Summary of surface tensions of various cationic surfactant samples

| Concentration (%) | 7 | 9 | 10 | 11 | 12 | 13 |
|---|---|---|---|---|---|---|
| 0.010 | 73.70 | 73.11 | 70.99 | 63.52 | 63.16 | 63.28 |
| 0.025 | 72.05 | 69.16 | 61.99 | 60.01 | 55.77 | 59.04 |
| 0.050 | 64.84 | 60.77 | 57.33 | 56.35 | 51.89 | 55.36 |
| 0.100 | 60.93 | 54.69 | 52.64 | 53.23 | 49.42 | 52.65 |
| 0.200 | 57.12 | 52.05 | 50.58 | 50.16 | 47.02 | 50.31 |
| 0.500 | 55.13 | 50.09 | 47.92 | 47.38 | 45.02 | 48.02 |
| 1.000 | NT | 49.38 | 47.48 | 46.58 | 44.22 | 47.78 |
| 1.500 | NT | NT | NT | NT | 43.46 | NT |
| 2.000 | NT | NT | NT | NT | 42.97 | NT |

Surface tension of various cationic surfactant samples is also shown graphically in FIG. 1.

Example 5: Synthesis of Multiple Quaternary Cationic Surfactants Based on a Reaction of a Polyalkyleneimine and a Substituted Alkyl Trialkyl Quaternary Ammonium Salt Polyethyleneimines (Lupasol G20 (50 wt % solution), 20 grams, 0.2204 mol —NH—) and 3-chloro-2-hydroxypropyl trimethylammonium chloride (69.06 grams, 60.0%, 0.2204 mol, (Sigma-Aldrich) were added to a 500 mL four-neck round bottom flask equipped with a mechanical stirrer, a thermometer, a temperature controller, a condenser, and an addition funnel. The reaction mixture was stirred and gently heated to 60° C. The pH value of the reaction was continuously monitored. Sodium hydroxide (50% aqueous solution) was slowly added to the reaction flask and the temperature was held constant at 60° C. The pH value of reaction solution was measured and was held constant above 7.5. The reaction temperature was raised to 85° C. and held constant for 5 hours. Compound 14 depicted below is a depiction of a generalized reaction product. The structure below depicts that all of the secondary and primary amines in the polyethyleneimine react with the 3-chloro-2-hydroxypropyl trimethylammonium chloride so that no secondary amines remain. There may be some amines that do not completely react leaving some secondary amines in the cationic polymer salt.

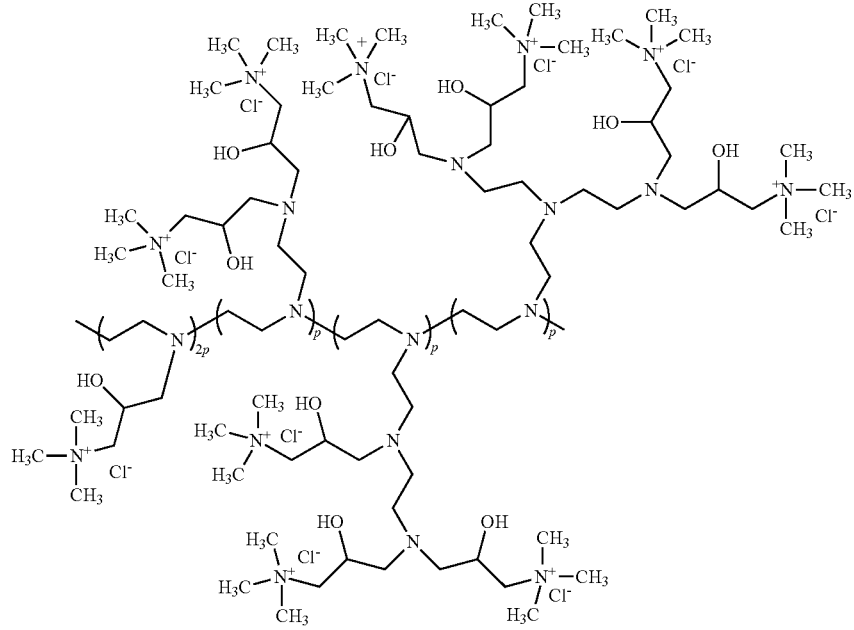

Compound 14

Multiple quaternary cationic surfactants with stearyl chains were synthesized by reacting polyethyleneimines branched (Sigma-Aldrich) with 3-chloro-2-hydroxypropyl-stearyldimethylammonium chloride (QUAB 426™ from Quab Chemicals, Saddle Brook, N.J.) and 3-chloro-2-hydroxypropyl trimethylammonium chloride (Sigma-Aldrich). Polyethyleneimines (40.0 grams (50%), 0.4206 mol —NH—) and 3-chloro-2-hydroxypropyl-stearyldimethylammonium chloride (47.15 grams, 38.5 wt. %, 0.0426 mol) and 3-chloro-2-hydroxypropyl trimethylammonium chloride (118.6 grams, (60%), 0.3785 mol) were charged to a 500 mL four-neck round bottom flask equipped with a mechanical stirrer, a thermometer, a temperature controller, a condenser, and an addition funnel. The reaction mixture was stirred and gently heated to 60° C. The pH value of the reaction was continuously monitored. Sodium hydroxide (50% aqueous solution) was slowly added to the reaction flask and the temperature was held constant at 60° C. The pH value of reaction solution was measured and was held constant above 7.5. The reaction temperature was raised to 85° C. and held constant for 5 hours. Surface tension, 41.55 mN/m @0.050 wt % aqueous solution. Compound 15 shows a generalized reaction product. Like Compound 14, there may be some secondary amines present if the reaction did not proceed to completion.

Polymeric quaternary compounds were synthesized according to the procedures described above to produce Compound 15 and Compound 16. Compound 16 had a weight average molecular weight of about 1300 gm/mol as measured by gel permeation chromatography. Compound 15 had a weight average molecular weight of about 25,000 gm/mol as measured by gel permeation chromatography. The variable "p" may range from about 10 to about $10^5$.

Compound 15

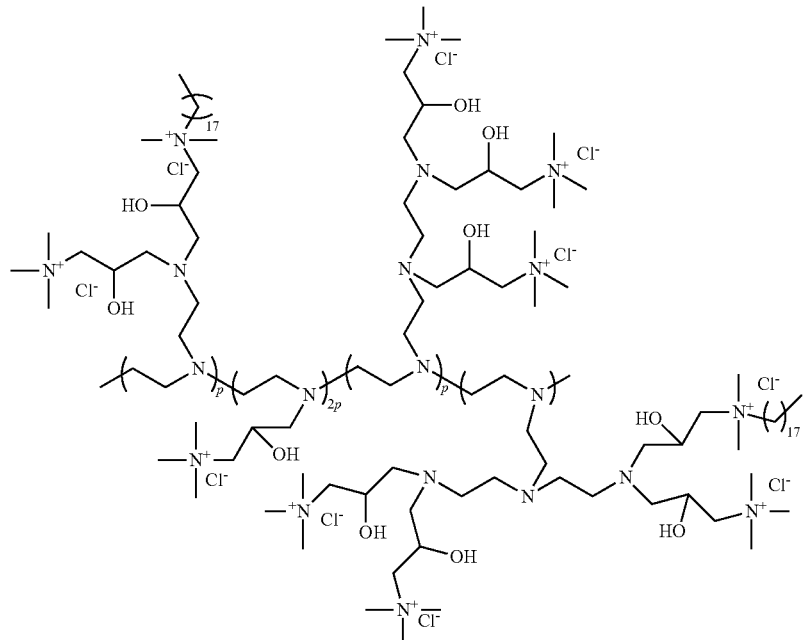

Compound 16

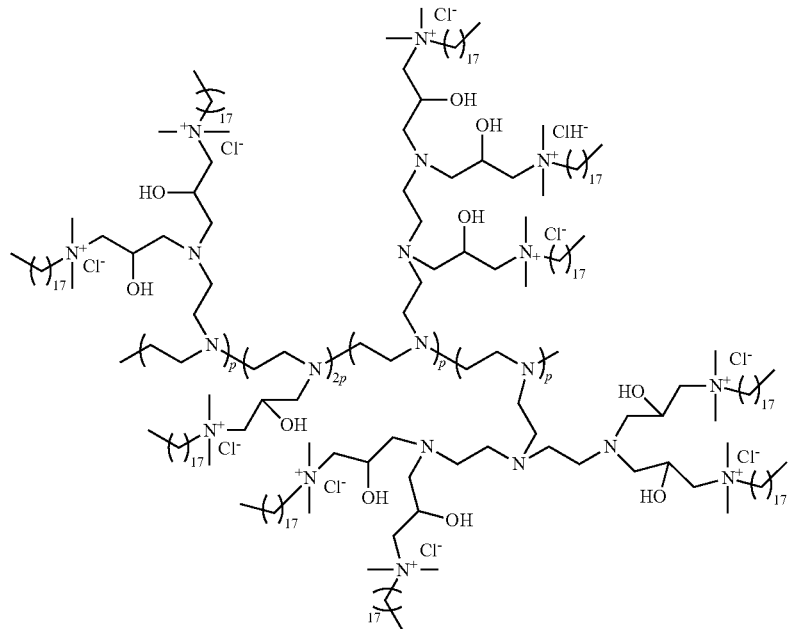

Example 6: Antimicrobial Effects of Cationic Polymer Salts

Antimicrobial efficiency of the synthesized compounds was tested using a non-oxidative antimicrobial efficiency test procedure according to ASTM method for microbiocide efficiency in cooling water (E645-02a, 2005). The bacteria used in the efficacy testing comprised a mixture of aerobic populations from more than 30 cooling systems in North America. The specific species were not identified. Those species were grown on $R_2A$ agar.

Figure 2:
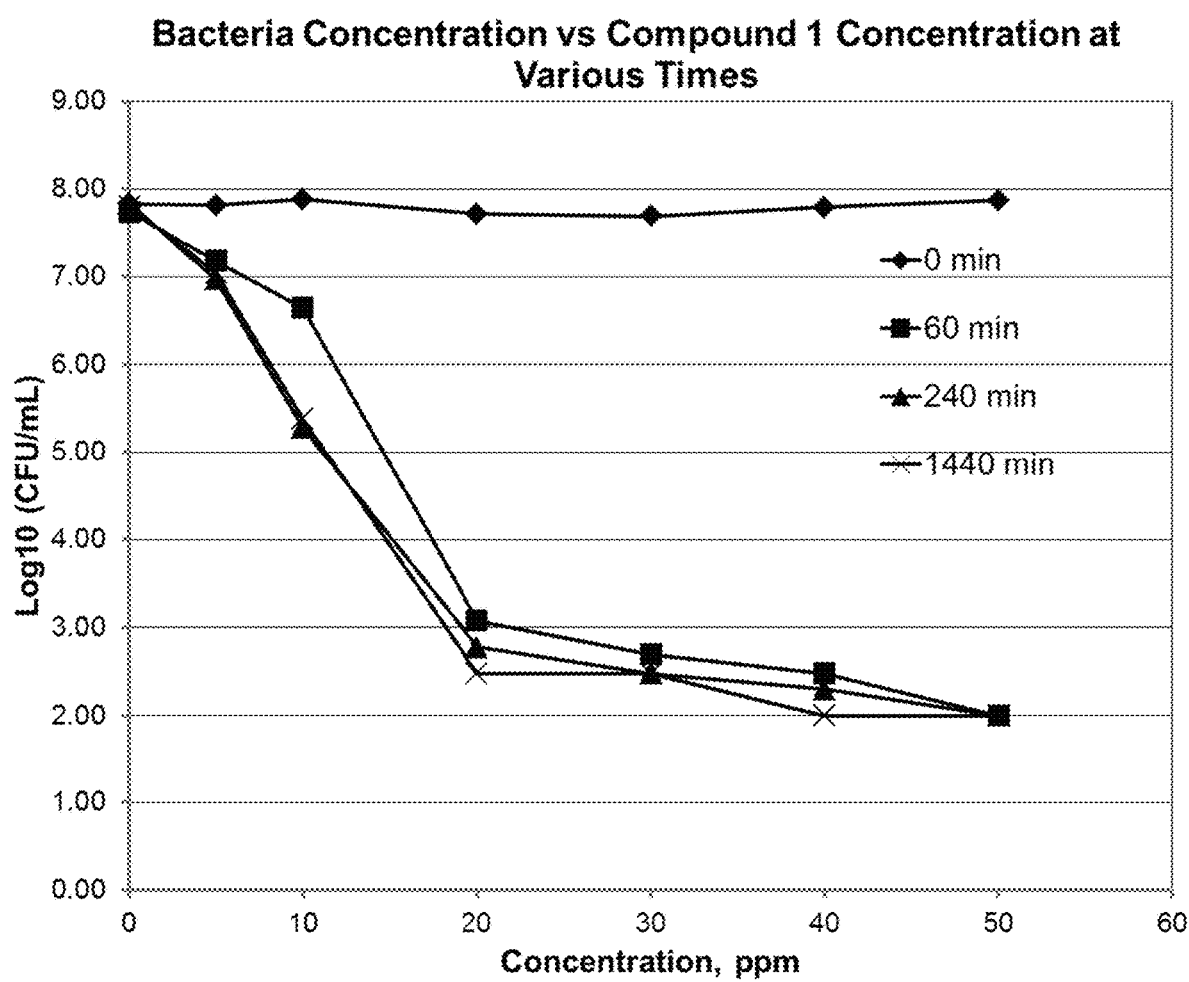
FIG. 2 shows effects of different concentrations of Compound 1 on bacteria reduction in cooling water at various times.

In one experiment, various concentrations (0 ppm, 5 ppm, 10 ppm, 20 ppm, 30 ppm, 40 ppm, and 50 ppm) of Compound 1 were applied to bacteria in water. The log 10 concentration in colony forming units (CFU/ml) was measured at four time points (0 min, 60 min, 240 min, and 1440 min). FIGS. 1 and 2 show that at a concentration of 5 ppm a single log 10 reduction was achieved. At about 20 ppm, a five log 10 reduction was observed at about 60 min, 240 min, and 1440 min.

Figure 3:
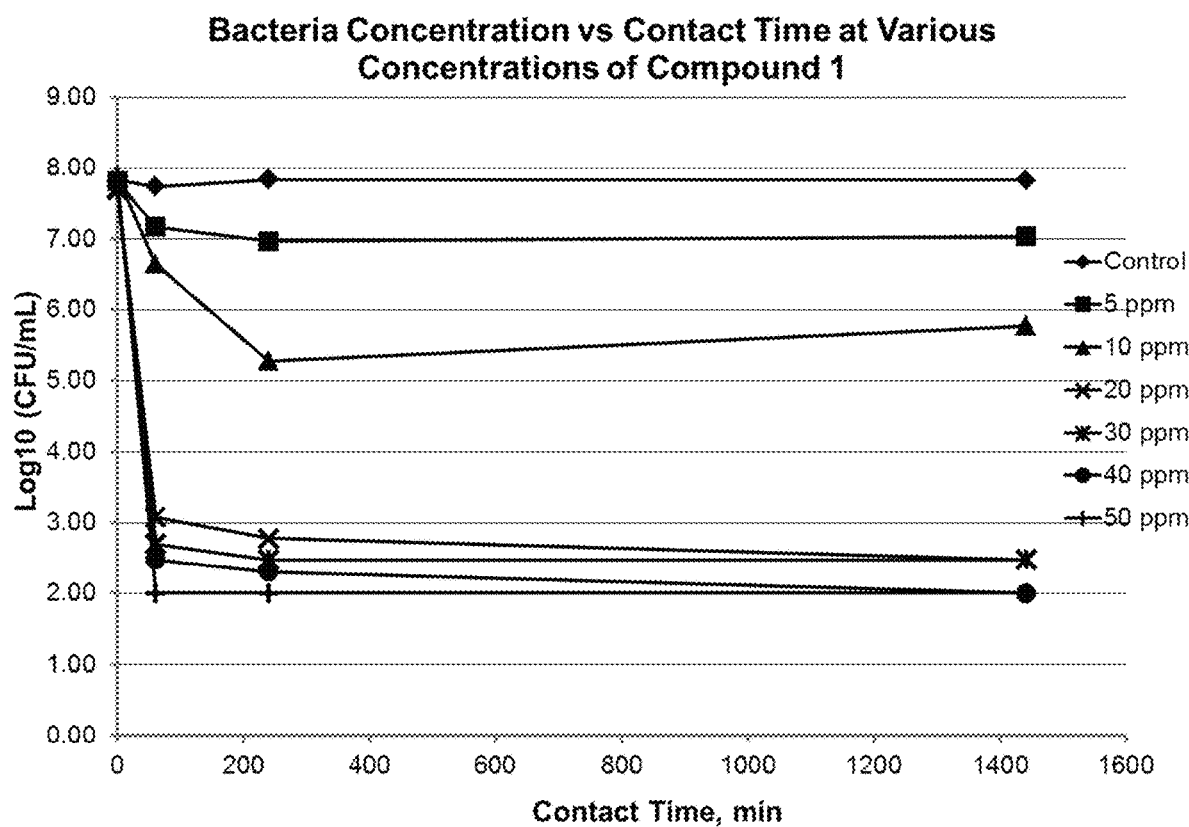
FIG. 3 shows the bacteria concentration as a function of contact time for various concentrations of Compound 1.

The microbial activity of Compounds 1-4 at a concentration of 50 ppm was tested according to the same procedure described above. FIG. 3 shows that all the compounds show significant reduction in CFUs after 60 min contact time. At about 5 ppm, Compound 2 showed some antimicrobial activity showing a single log 10 reduction in CFUs.

Figure 4:
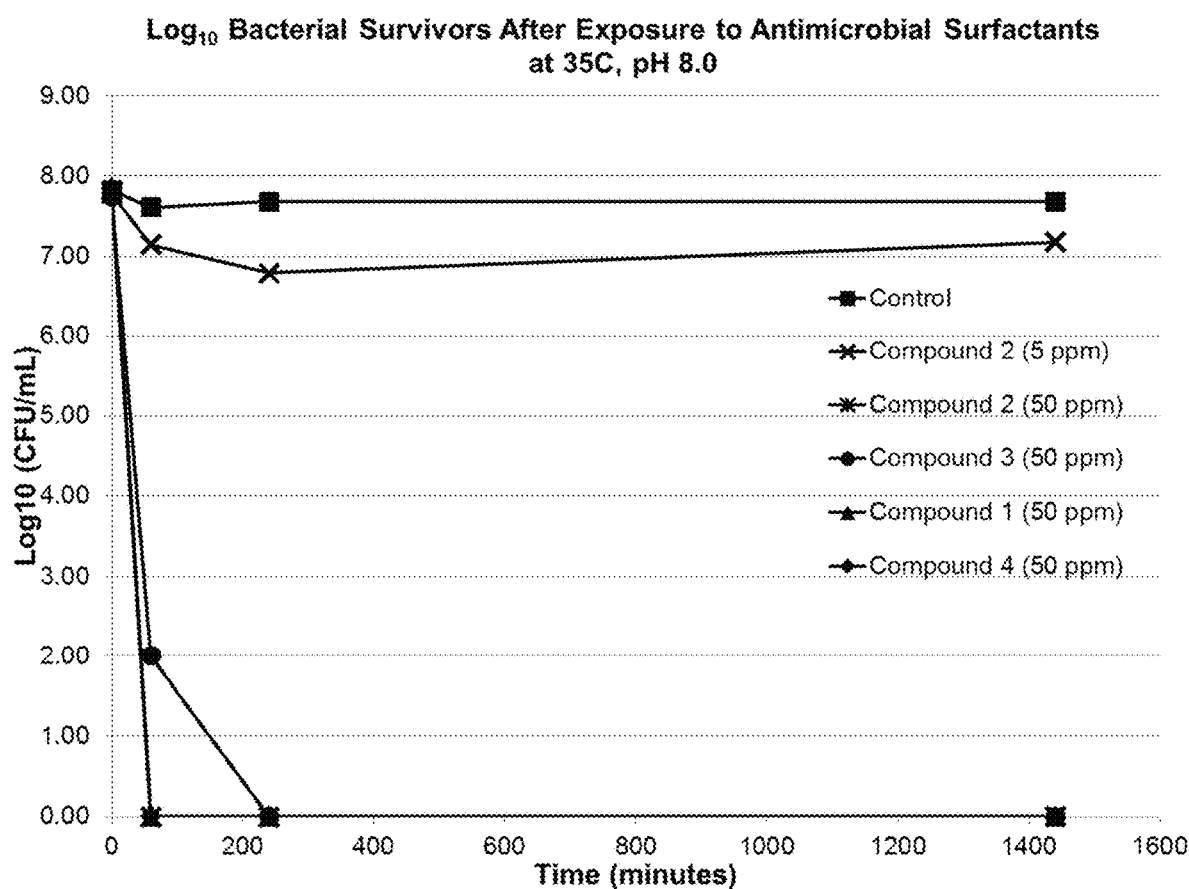
FIG. 4 shows the bacteria concentration as a function of time for Compounds 1-4.
Figure 5:
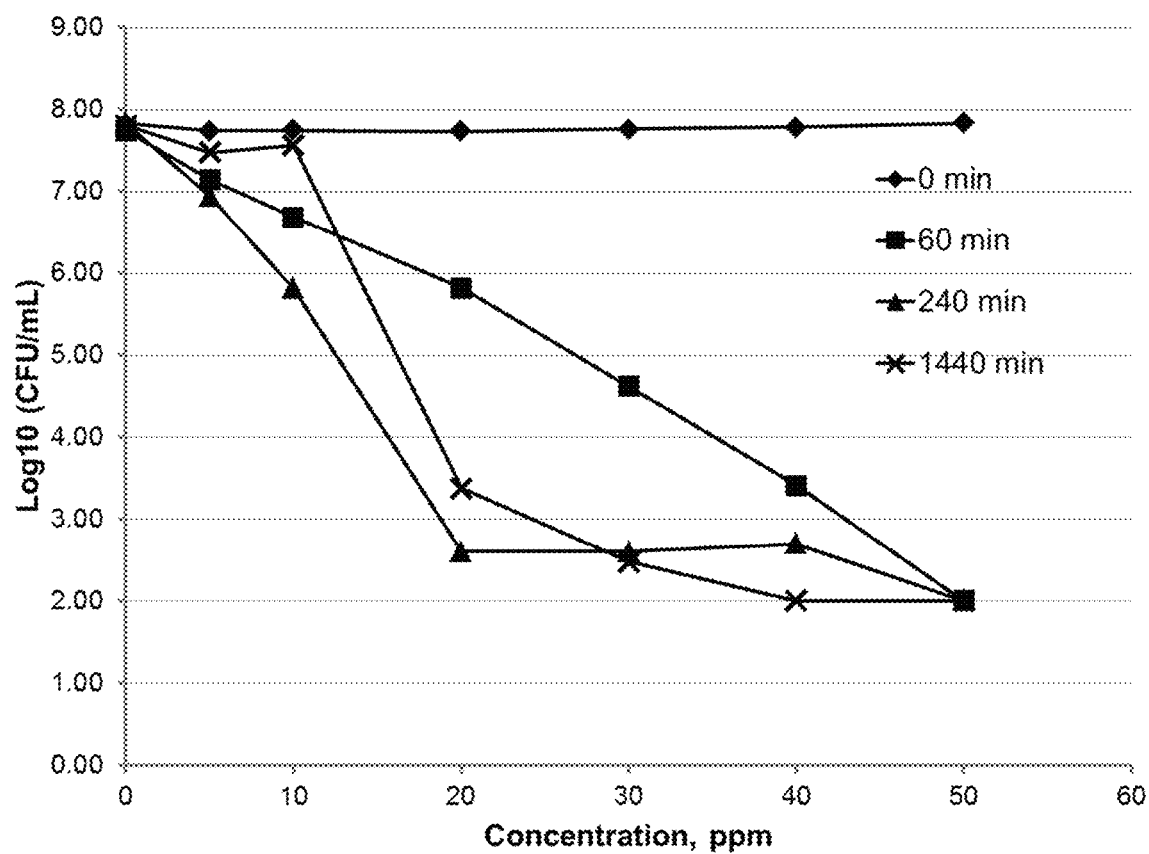
FIG. 5 shows effects of different concentrations of Compound 4 on bacteria concentration in cooling water at various times.
Figure 6:
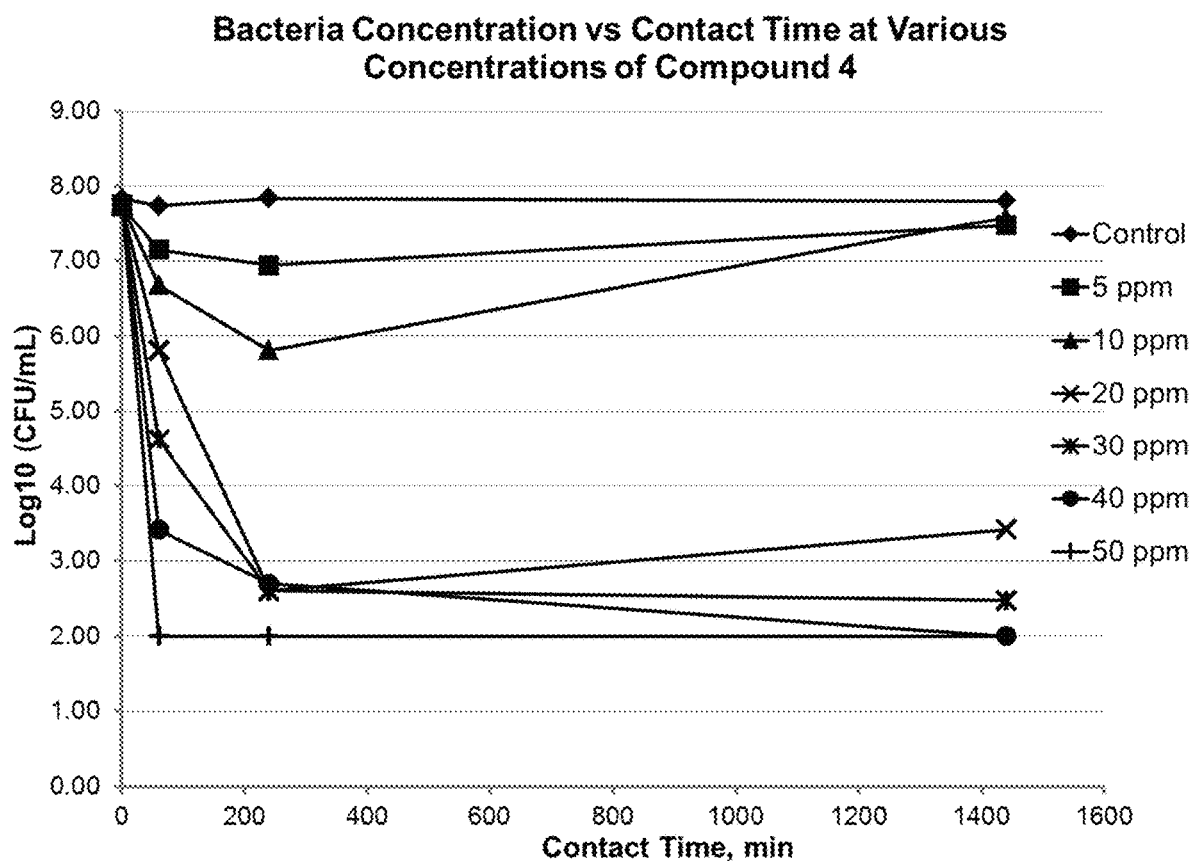
FIG. 6 shows bacteria concentration as a function of contact time for various concentrations of Compound 4.

The antimicrobial activity of Compound 4 was tested using the same procedures as described above. FIGS. 4 and 5 show significant antimicrobial activity at the tested concentrations.

Example 7: Cationic Polymer Salt Effect on Spores and Thermophiles

The effect of the compounds on bacterial spores or thermophiles was also tested. Compounds 1 and 4 were incubated separately with spores or thermophiles at a concentration of about 20 ppm, and the reduction in concentration was measured at four time points (See Table 3).

TABLE 3

Summary of anti-spore and anti-thermophile activity

| Contact Time (min) | Control (Log cfu/ml) | Compound 1 (Log cfu/ml) | Compound 1 Log Reduction | Compound 4 (Log cfu/ml) | Compound 4 Log Reduction |
|---|---|---|---|---|---|
| 0 | 2.49 | 2.41 | 0.08 | 2.53 | −0.04 |
| 60 | 2.34 | 1.85 | 0.5 | 1.6 | 0.74 |
| 240 | 2.48 | 1.48 | 1.0 | 0.00 | 2.48 |
| 1440 | 2.53 | 1.48 | 1.05 | 1.78 | 0.75 |

Example 8: Antimicrobial Efficacy of Single Quaternary Compounds and Multi-Quaternary Cationic Polymers Biofilm reduction experiments were conducted to test the efficacy of multi-quaternary cationic polymers compared to single quaternary compounds. Two different compositions were prepared containing single quaternary compounds: a composition (Single Quat 1) comprising about 50% by weight bisoctyl dimethyl ammonium chloride (CAS #5538-94-3) and about 5-10% by weight glycerin; and a composition (Single Quat 2) comprising about 50% by weight didecyl-dimethyl ammonium chloride (CAS #7173-51-5) and about 10-30% by weight ethanol. The test bacteria comprised a collection of aerobic bacteria from 30 water samples in cooling towers across North America. Different concentrations of cationic polymer salts and single quaternary compounds were tested ranging from about 0.8 ppm to about 1000 ppm. Using the biofilm inhibition test protocols, the absorbed stains were extracted and absorbance was measured at 590 nm. The biofilm reduction was calculated by comparing the absorbance of treated vs untreated controls, then averaged over six replicates.

Compounds 7 and 9 were compared the Single Quat 2 composition described above. Tables 4 and 5 show that at concentrations as low as about 12 ppm that Compound 7 reduced biofilms to a greater extent than the Single Quat 2 composition. Compound 7 also had biofilm reduction of about 12 to about 65% in from about 0.8 ppm to about ppm concentration range. Compound 9 achieved greater than 95% reduction in biofilm formation at concentrations about 100 ppm. The compounds show significant advantages over traditional products.

TABLE 4

Biofilm reduction of Compound 7 compared to Single Quat 2

| Active Conc. ppm | Single Quat 2 % | Compound 7 % | $\frac{(\text{Comp. 7} - \text{Single Quat 2}) * 100}{\text{Single Quat 2}}$ % |
|---|---|---|---|
| 1000.0 | 60.1 | 98.4 | 63.7 |
| 500.0 | 92.0 | 97.8 | 6.3 |
| 250.0 | 84.2 | 97.1 | 15.3 |
| 125.0 | −6.8 | 96.6 | 1517.3 |
| 100.0 | −15.6 | 79.3 | 608.5 |
| 62.0 | 65.4 | 96.6 | 47.6 |
| 50.0 | 80.4 | 93.0 | 15.7 |
| 31.0 | 81.6 | 94.7 | 16.0 |
| 25.0 | 80.3 | 90.6 | 12.9 |
| 16.0 | 81.7 | 90.6 | 10.9 |
| 12.0 | 52.5 | 65.1 | 24.2 |
| 8.0 | 69.3 | 54.9 | −20.8 |
| 6.0 | 8.0 | 23.5 | 195.0 |
| 3.0 | 34.5 | 46.7 | 35.5 |
| 1.6 | −5.7 | 12.7 | 321.3 |
| 0.8 | 11.1 | 22.9 | 106.8 |

TABLE 5

Biofilm reduction of Compound 9 compared to Single Quat 2

| Active Conc. ppm | Single Quat 2 % | Compound 9 % | $\frac{(\text{Comp. 9} - \text{Single Quat 2}) * 100}{\text{Single Quat 2}}$ % |
|---|---|---|---|
| 1000.0 | 74.7 | 99.6 | 33.5 |
| 500.0 | 80.5 | 99.6 | 23.7 |
| 250.0 | 64.1 | 99.5 | 55.3 |
| 125.0 | 52.4 | 98.9 | 88.6 |
| 100.0 | 68.6 | 97.3 | 41.9 |
| 62.0 | 91.1 | 90.7 | −0.4 |
| 50.0 | 92.2 | 77.6 | −15.9 |
| 31.0 | 95.4 | 46.9 | −50.8 |
| 25.0 | 91.3 | 76.8 | −15.9 |
| 16.0 | 93.5 | 79.0 | −15.5 |
| 12.0 | 81.6 | 70.9 | −13.2 |
| 8.0 | 68.5 | 62.6 | −8.6 |
| 6.0 | 51.1 | 45.4 | −11.1 |
| 3.0 | 72.5 | 41.2 | −43.2 |
| 1.6 | 39.7 | 35.9 | −9.6 |
| 0.8 | −9.6 | 20.5 | 314.7 |

Example 9: Biofilm Reduction Using Polymeric Quats Compared to Single Quat 2

Figure 7:
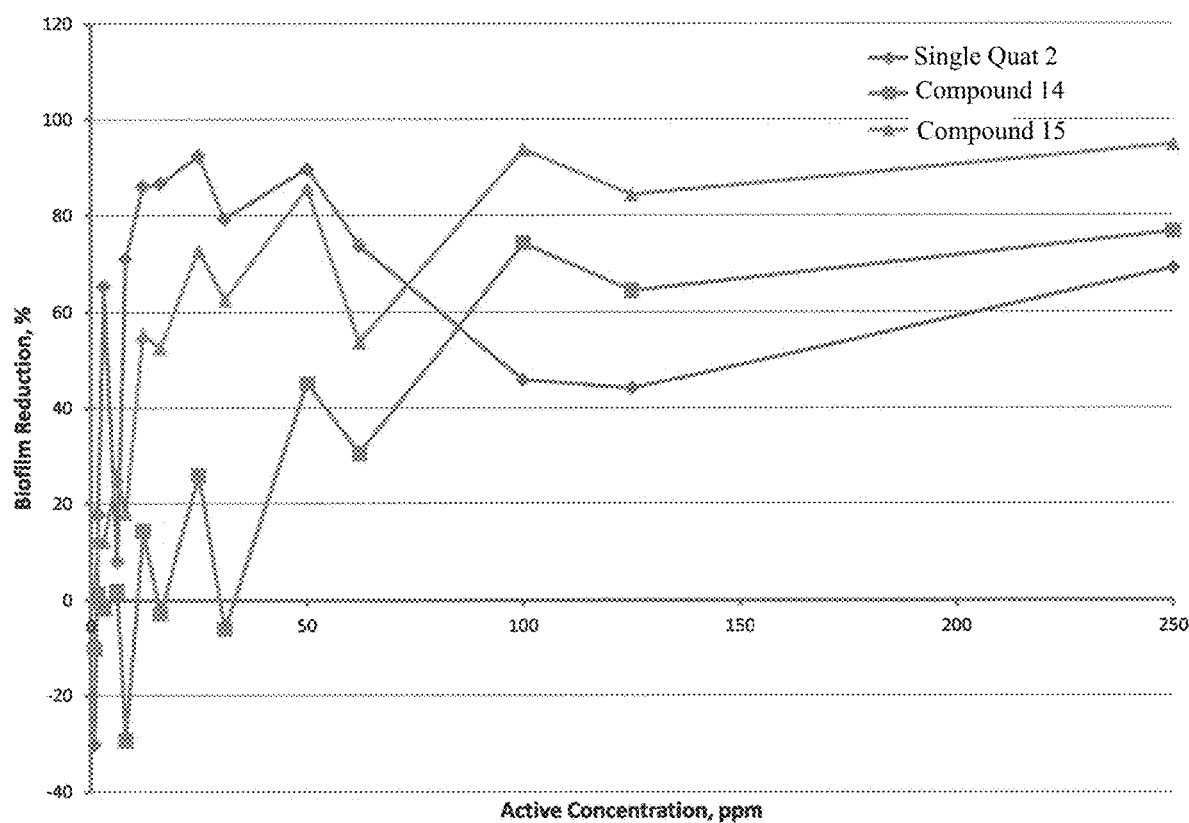
FIG. 7 shows biofilm reduction of a single quat compound compared to polymer quaternary compounds.
Figure 8:
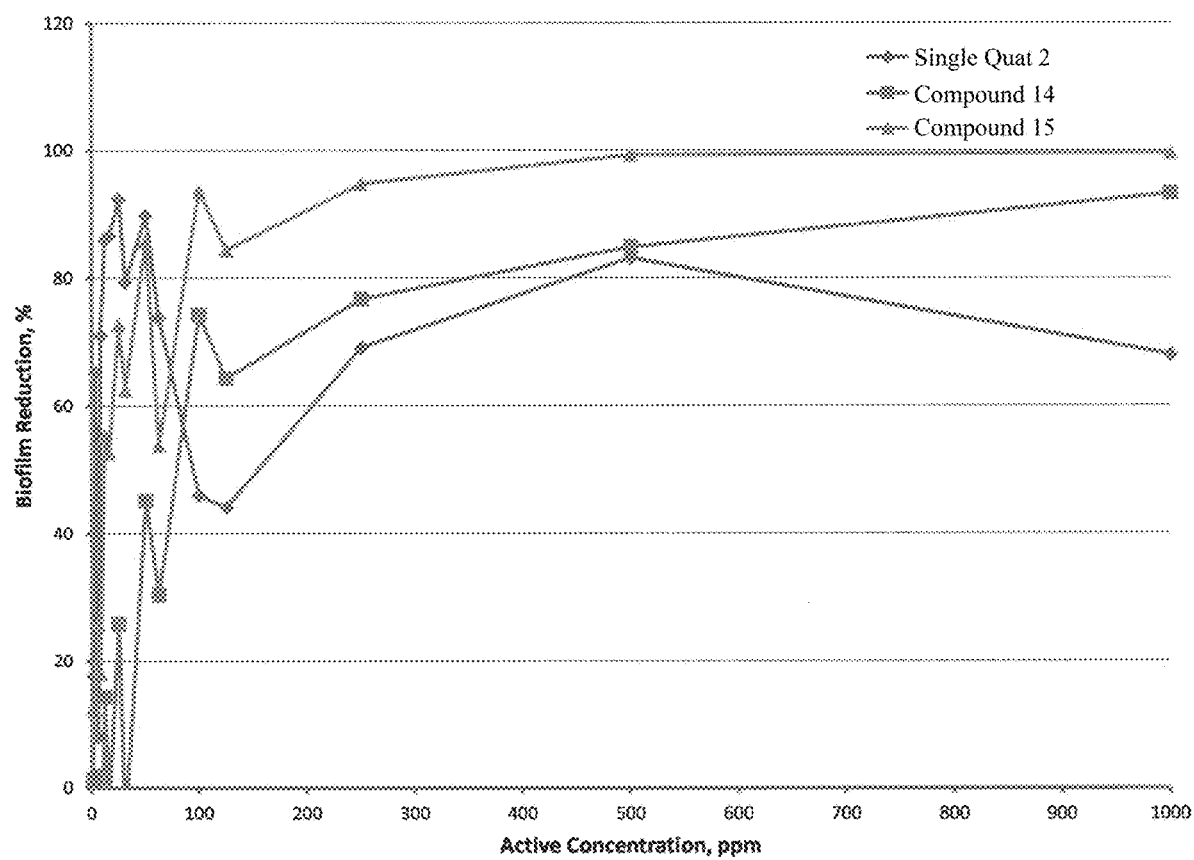
FIG. 8 shows biofilm reduction of a single quat compound compared to polymer quaternary compounds.

A biofilm assay was performed using a modified version of ASTM E2799-11. Single Quat 2 was compared to Compound 15. Table 6 shows the percent change in the biofilm compared the Single Quat 2. FIG. 7 and FIG. 8 show a graphical representation of biofilm reduction of Compound 15 compared to Single Quat 2 and Compound 16.

TABLE 6

Biofilm reduction of Compound 15 compared to Single Quat 2

| Active Conc. ppm | Single Quat 2 % | Compound 15 % | $\frac{(\text{Comp. 15} - \text{Single Quat 2}) * 100}{\text{Single Quat 2}}$ % |
|---|---|---|---|
| 1000.0 | 68.0 | 99.6 | 46.5 |
| 500.0 | 83.2 | 99.3 | 19.4 |
| 250.0 | 69.2 | 94.8 | 37.1 |
| 125.0 | 44.1 | 84.4 | 91.4 |

TABLE 6-continued

Biofilm reduction of Compound 15 compared to Single Quat 2

| Active Conc. ppm | Single Quat 2 % | Compound 15 % | (Comp. 15 − Single Quat 2) * 100 / Single Quat 2 % |
|---|---|---|---|
| 100.0 | 45.9 | 93.8 | 104.2 |
| 62.0 | 73.8 | 53.8 | −27.1 |
| 50.0 | 89.8 | 85.8 | −4.5 |
| 31.0 | 79.4 | 62.6 | −21.1 |
| 25.0 | 92.4 | 72.8 | −21.2 |
| 16.0 | 86.7 | 52.7 | −39.2 |
| 12.0 | 86.1 | 55.5 | −35.6 |
| 8.0 | 71.0 | 18.0 | −74.6 |
| 6.0 | 8.2 | 25.9 | 217.6 |
| 3.0 | 65.3 | 12.3 | −81.2 |
| 2 | 17.8 | 12.7 | −28.7 |
| 1 | −30.0 | −0.1 | −99.5 |

Single Quat 2 was compared to Compound 16 in a biofilm assay. Table 7 shows the percent change in the biofilm compared the Single Quat 2. FIG. 7 and FIG. 8 show a graphical representation of biofilm reduction of Compound 16 compared to Single Quat 2 and Compound 15.

TABLE 7

Biofilm reduction of Compound 16 compared to Single Quat 2

| Active Conc. ppm | Single Quat 2 % | Compound 16 % | (Comp. 16 − Single Quat 2) * 100 / Single Quat 2 % |
|---|---|---|---|
| 1000.0 | 74.7 | 93.3 | 25.0 |
| 500.0 | 80.5 | 84.8 | 5.3 |
| 250.0 | 64.1 | 76.7 | 19.7 |
| 125.0 | 52.4 | 64.4 | 22.8 |
| 100.0 | 68.6 | 74.3 | 8.4 |
| 62.0 | 91.1 | 30.4 | −66.6 |
| 50.0 | 92.2 | 45.2 | −51.0 |
| 31.0 | 95.4 | −6.0 | −106.3 |
| 25.0 | 91.3 | 25.9 | −71.6 |
| 16.0 | 93.5 | −2.7 | −102.9 |
| 12.0 | 81.6 | 14.4 | −82.3 |
| 8.0 | 68.5 | −29.3 | −142.8 |
| 6.0 | 51.1 | 1.9 | −96.3 |
| 3.0 | 72.5 | −1.7 | −102.3 |

TABLE 7-continued

Biofilm reduction of Compound 16 compared to Single Quat 2

| Active Conc. ppm | Single Quat 2 % | Compound 16 % | (Comp. 16 − Single Quat 2) * 100 / Single Quat 2 % |
|---|---|---|---|
| 1.6 | 39.7 | 1.4 | −96.5 |
| 0.8 | −9.6 | −10.0 | −4.9 |

Example 10: Corrosion Bubble Cell Tests of Pentaquaternary Cationic Polymer Salts Cationic polymer salts were evaluated for corrosion performance as compared to a $C_{12}$-$C_{18}$ alkyl dimethyl benzyl ammonium chloride via a bubble test procedure. The bubble test simulates low flow areas where little or no mixing of water and oil occurs. The test was conducted using brine (80% of the brine being 3% sodium chloride brine and 20% of the brine being a hydrocarbon containing 75% LVT-200 kerosene oil and 25% xylene). The brine was placed into kettles and purged with carbon dioxide. The brine was continually purged with carbon dioxide to saturate the brine prior to starting the test. After the test began, the test cell was blanketed with carbon dioxide one hour prior to electrode insertion and through the duration of the test to maintain saturation. The kettles were stirred at 150 revolutions per minute (rpm) for the duration of the test to maintain thermal equilibrium at 80° C. The corrosion rate was measured by Linear Polarization Resistance (LPR) techniques. The working electrode used was carbon steel. The counter and reference electrodes were both 1018 carbon steel. The electrodes were all cleaned and polished prior to testing. Data were collected for three hours before 20 ppm of each of the compositions (containing 2 ppm of each of various pentaquaternary cationic polymer salts or the comparative $C_{12}$-$C_{18}$ alkyl dimethyl benzyl ammonium chloride and 1% 2-mercaptoethanol (2ME) as synergist in an organic solvent) was dosed into its respective cell. Data were collected overnight. A low concentration of the compositions was used to differentiate between the compositions.

The results of the bubble test are shown in Table 8, wherein ppm is parts per million, CI is corrosion inhibitor, mpy is mils per year, and the Compound No. is as listed in Table 1 and/or depicted in Example 3.

TABLE 8

Bubble test results

| Cationic Polymer Salt or Comparative Cationic Compound | Dosage of Cationic Polymer Salt or Compound (ppm) | Synergist | Average Baseline Corrosion Rate Before Cationic Polymer Salt or Compound Addition (mpy) | Inhibited Corrosion Rate 15 h After Cationic Polymer Salt or Compound Addition (mpy) | % Protection |
|---|---|---|---|---|---|
| None | 0 | None | 260 | 500 | −92 |
| $C_{12}$-$C_{18}$ alkyl dimethyl benzyl ammonium chloride (Comparative) | 2 | 1% 2ME | 236 | 147 | 38 |
| Compound 1 (4 lauryl dimethyl & 1 trimethyl quats) | 2 | 1% 2ME | 223 | 130 | 42 |
| Compound 7 (1 stearyl dimethyl & 1 trimethyl quats) | 2 | 1% 2ME | 251 | 90 | 64 |

TABLE 8-continued

Bubble test results

| Cationic Polymer Salt or Comparative Cationic Compound | Dosage of Cationic Polymer Salt or Compound (ppm) | Synergist | Average Baseline Corrosion Rate Before Cationic Polymer Salt or Compound Addition (mpy) | Inhibited Corrosion Rate 15 h After Cationic Polymer Salt or Compound Addition (mpy) | % Protection |
|---|---|---|---|---|---|
| Compound 9 (2 stearyl dimethyl & 3 trimethyl quats) | 2 | 1% 2ME | 226 | 90 | 60 |
| Compound 11 (4 stearyl dimethyl & 1 trimethyl quat) | 2 | 1% 2ME | 228 | 55 | 76 |
| Compound 12 (5 stearyl dimethyl quats) | 2 | 1% 2ME | 255 | 115 | 55 |

Example 11: Corrosion Bubble Cell Tests of Hexaquaternary Cationic Polymer Salts Corrosion bubble cell tests were performed according to the method of Example A1 to evaluate a hexaquaternary cationic polymer salt for corrosion performance as compared to a $C_{12}$-$C_{18}$ alkyl dimethyl benzyl ammonium chloride. Data were collected for three hours before 20 ppm of each of the compositions (containing 2 ppm of a hexaquaternary cationic polymer salt or the comparative $C_{12}$-$C_{18}$ alkyl dimethyl benzyl ammonium chloride and 1% 2ME as synergist in an organic solvent) was dosed into its respective cell. Data were collected overnight. A low concentration of the compositions was used to differentiate between the compositions.

The results of the bubble test are shown in Table 9, wherein ppm is parts per million, CI is corrosion inhibitor, mpy is mils per year, and the Compound No. is as listed in Table 1 and/or depicted in Example 3.

TABLE 9

Bubble test results

| Cationic Polymer Salt or Comparative Cationic Compound | Dosage of Cationic Polymer Salt or Compound (ppm) | Synergist | Average Baseline Corrosion Rate Before Cationic Polymer Salt or Compound Addition (mpy) | Inhibited Corrosion Rate 15 h After Cationic Polymer Salt or Compound Addition (mpy) | % Protection |
|---|---|---|---|---|---|
| None | 0 | None | 260 | 500 | −92 |
| $C_{12}$-$C_{18}$ alkyl dimethyl benzyl ammonium chloride (Comparative) | 2 | 1% 2ME | 236 | 147 | 38 |
| Compound 13 (6 stearyl dimethyl quats) | 2 | 1% 2ME | 239 | 114 | 52 |

Example 12: Corrosion Bubble Cell Tests of Polyethyleneimine-Based Cationic Polymer Salts Cationic polymer salts were evaluated for corrosion performance as compared to a $C_{12}$-$C_{18}$ alkyl dimethyl benzyl ammonium chloride via a bubble test procedure. The bubble test simulates low flow areas where little or no mixing of water and oil occurs. The test was conducted using brine (80% of the brine being 3% sodium chloride brine and 20% of the brine being a hydrocarbon containing 75% LVT-200 kerosene oil and 25% xylene). The brine was placed into kettles and purged with carbon dioxide. The brine was continually purged with carbon dioxide to saturate the brine prior to starting the test. After the test began, the test cell was blanketed with carbon dioxide one hour prior to electrode insertion and through the duration of the test to maintain saturation. The kettles were stirred at 150 revolutions per minute (rpm) for the duration of the test to maintain thermal equilibrium at 80° C. The corrosion rate was measured by Linear Polarization Resistance (LPR) techniques. The working electrode used was carbon steel. The counter and reference electrodes were both 1018 carbon steel. The electrodes were all cleaned and polished prior to testing. Data were collected for six hours before 20 ppm of each of the compositions (containing 2 ppm of each of various polyethyleneimine-based cationic polymer salts or the comparative $C_{12}$-$C_{18}$ alkyl dimethyl benzyl ammonium chloride and 1% 2-mercaptoethanol (2ME) as synergist in an organic solvent) was dosed into its respective cell. However, for the comparative composition, data was only collected three hours before addition of the compositions. Data were collected overnight. A low concentration of the compositions was used to differentiate between the compositions.

The results of the bubble test are shown in Table 10, wherein ppm is parts per million, CI is corrosion inhibitor, mpy is mils per year, and the Compound No. is as depicted in Example 5.

TABLE 10

Bubble test results

| Cationic Polymer Salt or Comparative Cationic Compound | Dosage of Cationic Polymer Salt or Compound (ppm) | Synergist | Average Baseline Corrosion Rate Before Cationic Polymer Salt or Compound Addition (mpy) | Inhibited Corrosion Rate 15 h After Cationic Polymer Salt or Compound Addition (mpy) | % Protection |
|---|---|---|---|---|---|
| None | 0 | None | 260 | 500 | −92 |
| $C_{12}$-$C_{18}$ alkyl dimethyl benzyl ammonium chloride (Comparative) | 2 | 1% 2ME | 236 | 147 | 38 |
| Compound 14 | 2 | 1% 2ME | 257 | 138 | 46 |
| Compound 15 | 2 | 1% 2ME | 255 | 134 | 48 |

It is expected that the addition of more stearyl groups to the Compound 15 will further reduce the corrosion rate and provide increased protection as compared to Compound 15.

Any composition disclosed herein may comprise, consist of, or consist essentially of any of the compounds/components disclosed herein. In accordance with the present disclosure, the phrases "consist essentially of," "consists essentially of," "consisting essentially of," and the like limit the scope of a claim to the specified materials or steps and those materials or steps that do not materially affect the basic and novel characteristic(s) of the claimed invention.

As used herein, the term "about" refers to the cited value being within the errors arising from the standard deviation found in their respective testing measurements, and if those errors cannot be determined, then "about" refers to within 10% of the cited value.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a surfactant" is intended to include "at least one surfactant" or "one or more surfactants."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A cationic polymer salt comprising a reaction product derived from a reaction of a polyamine or a polyalkyleneimine and a substituted alkyl trialkyl quaternary ammonium salt of formula (I):

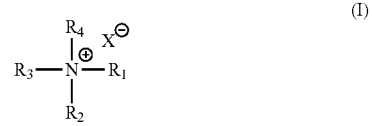

wherein
each $X^-$ is independently an anion;
$R_1$ is $C_1$-$C_6$ alkylene substituted with a hydroxyl or —$OR_5$ and an $X^-$ end group;
$R_2$, $R_3$, and $R_4$ are each independently $C_1$-$C_{22}$ alkyl or $C_7$-$C_{22}$ arylalkyl; and
$R_5$ is $C_1$-$C_6$ alkyl;
wherein any one of the following:
(A) the cationic polymer salt has no substitutions within its main chain, no alkyl-quaternized ammonium within its main chain, and comprises at least 4 quaternary ammonium groups; or
(B) the cationic polymer salt has one or more terminal tertiary amine groups having the formula (IV):

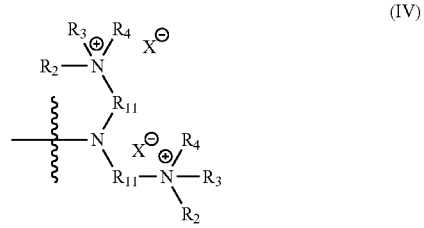

wherein $R_{11}$ is $R_1$ without the $X^-$ end group, and either:
the polymer salt has no substitutions within its main chain or at least 1 of $R_2$, $R_3$, and $R_4$ is a $C_9$-$C_{22}$ alkyl group; or
(C) $R_2$ and $R_3$ are $C_6$-$C_{22}$ alkyl or $C_7$-$C_{22}$ arylalkyl and $R_4$ is methyl.

2. The polymer salt of claim 1, wherein $X^-$ is selected from the group consisting of chloride, bromide, fluoride, iodide, acetate, aluminate, cyanate, cyanide, dihydrogen phosphate, dihydrogen phosphite, formate, hydrogen carbonate, hydrogen oxalate, hydrogen sulfate, hydroxide, metaniobate, metavanadate, nitrate, nitrite, thiocyanate, and any combination thereof.

3. The polymer salt of claim 2, wherein $X^-$ is chloride or bromide.

4. The polymer salt of claim 1, wherein $R_1$ is $C_2$-$C_3$ alkylene substituted with hydroxyl.

5. The polymer salt of claim 1, wherein $R_2$, $R_3$, and $R_4$ are independently $C_1$-$C_{22}$ alkyl.

6. The polymer salt of claim 1, wherein $R_2$ is $C_6$-$C_{22}$ alkyl or $C_7$-$C_{22}$ arylalkyl and $R_3$ and $R_4$ are methyl.

7. The polymer salt of claim 1, wherein $R_2$ and $R_3$ are $C_6$-$C_{22}$ alkyl or $C_7$-$C_{22}$ arylalkyl and $R_4$ is methyl.

8. The polymer salt of claim 5, wherein $R_2$, $R_3$, and $R_4$ are methyl.

9. The polymer salt of claim 1, wherein the substituted alkyl trialkyl quaternary ammonium salt comprises 3-chloro-2-hydroxypropyl-trimethylammonium chloride, 3-chloro-2-hydroxypropyl-dodecyl-dimethylammonium chloride, 3-chloro-2-hydroxypropyl-stearyl-dimethylammonium chloride, or any combination thereof.

10. The polymer salt of claim 1, wherein the polyamine has the formula (II):

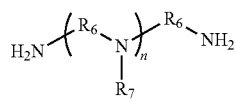
(II)

wherein
n is an integer from 0 to 100;
each $R_6$ is independently $C_2$-$C_6$ alkylene; and
each $R_7$ is independently hydrogen or —$R_6$—$NH_2$, —$R_6$—NH—$R_6$—$NH_2$, or —$R_6$—N—($R_6$—$NH_2$)$_2$.

11. The polymer salt of claim 10, wherein n is selected from the group consisting of 1 to 50, 1 to 10, 1 to 5, 0 to 50, 0 to 10, and 0 to 5.

12. The polymer salt of claim 10, wherein $R_6$ is a $C_2$-$C_3$ alkyl.

13. The polymer salt of claim 12, wherein $R_6$ is ethyl.

14. The polymer salt of claim 1, wherein (A) the cationic polymer salt has no substitutions within its main chain, no alkyl-quaternized ammonium within its main chain, and comprises at least 4 quaternary ammonium groups.

15. The polymer salt of claim 1, wherein (B) the cationic polymer salt has one or more terminal tertiary amine groups having the formula (IV):

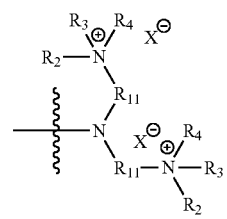
(IV)

wherein $R_{11}$ is $R_1$ without the $X^-$ end group, and either: the polymer salt has no substitutions within its main chain or at least 1 of $R_2$, $R_3$, and $R_4$ is a $C_9$-$C_{22}$ alkyl group.

16. The polymer salt of claim 1, wherein (C) $R_2$ and $R_3$ are $C_6$-$C_{22}$ alkyl or $C_7$-$C_{22}$ arylalkyl and $R_4$ is methyl.

17. The polymer salt of claim 1, wherein the polyamine comprises an alkyleneamine, the alkyleneamine comprising ethylenediamine, diethylenetriamine, triethylenetetraamine, diethylenetriamine, triethylenetetramine, tetraethylenepentamine, pentaethylenehexamine, hexaethyleneheptamine, or a combination thereof.

18. The polymer salt of claim 1, wherein the polyalkyleneimine comprises ethyleneimine; propyleneimine; butyleneimine; pentyleneimine; hexyleneimine; heptyleneimine; branched, linear, or dendrimer polyethyleneimine; or any combination thereof.

19. The polymer salt of claim 1, wherein the molar ratio of the polyamine or polyalkyleneimine to the substituted alkyl trialkyl quaternary ammonium salt ranges from 1:1 to 1:100, 1:1 to 1:50, 1:1 to 1:25, 1:1 to 1:10, 1:1 to 1:5, or 1:1 to 1:2.

20. A cationic polymer salt having the formula (III):

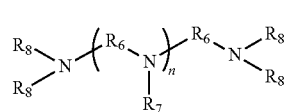
(III)

wherein
each $R_6$ is independently $C_2$-$C_6$ alkylene;
each $R_7$ is independently —$R_8$, —$R_6$—N($R_8$)$_2$, —$R_6$—N($R_8$)—$R_6$—N($R_8$)$_2$, or —$R_6$—N—($R_6$—N($R_8$)$_2$)$_2$;
each $R_8$ is

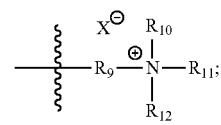

each $R_9$ is independently $C_2$-$C_6$ alkylene substituted with hydroxyl or —$OR_{13}$;
$R_{10}$, $R_{11}$, and $R_{12}$ are each independently $C_1$-$C_{22}$ alkyl or $C_7$-$C_{22}$ arylalkyl;
$R_{13}$ is $C_1$-$C_6$ alkyl;
n is an integer from 1 to 100; and
each $X^-$ is independently an anion.

21. The polymer salt of claim 20, wherein n is from 1 to 50 or 1 to 25.

22. The polymer salt of claim 20, wherein each $R_6$ and $R_9$ is independently $C_2$-$C_3$ alkylene.

23. The polymer salt of claim 22, wherein each $R_6$ is ethylene.

24. The polymer salt of claim 20, wherein each $R_9$ is hydroxypropylene; $R_{10}$ and $R_{11}$ are methyl; and each $R_{12}$ is independently methyl or $C_8$-$C_{22}$ alkyl.

25. The polymer salt of claim 24, wherein at least one $R_{12}$ is $C_8$-$C_{22}$ alkyl.

26. The polymer salt of claim 20, wherein the polymer salt is any one of Compounds 1 through 13:
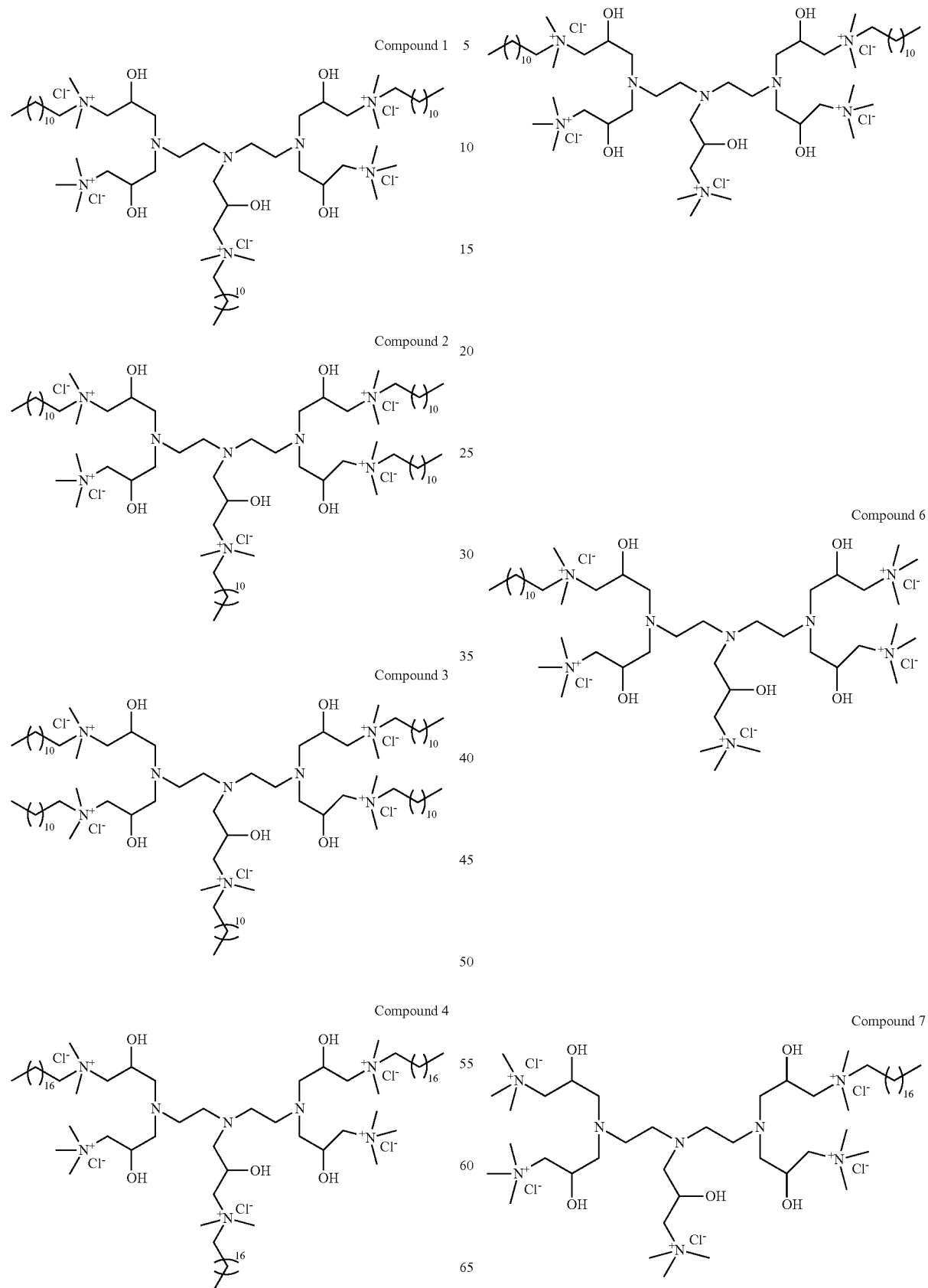

Compound 8
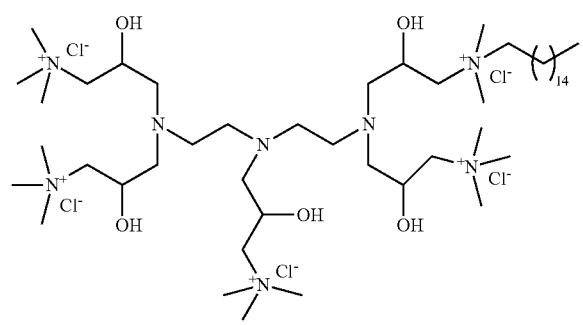
Compound 11
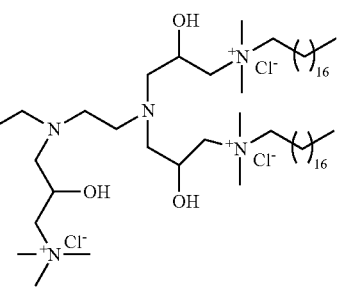
Compound 9
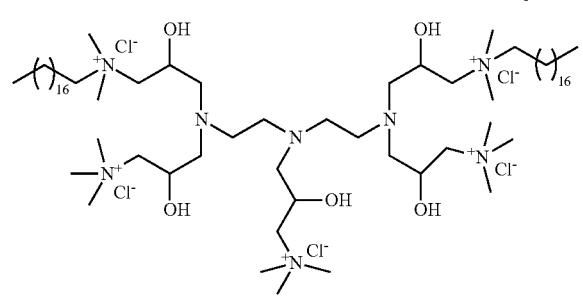
Compound 12
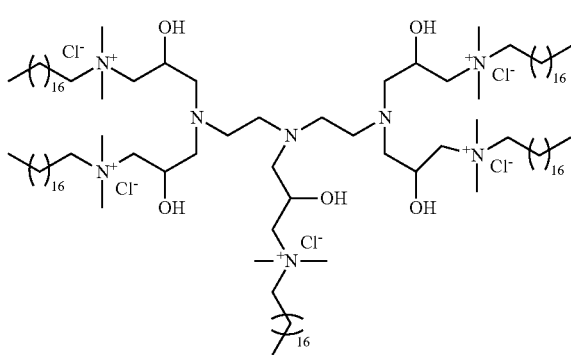
Compound 10
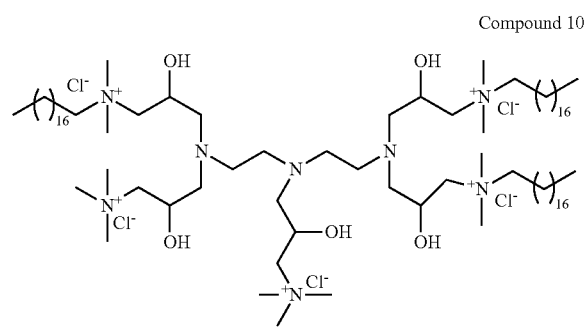
Compound 13
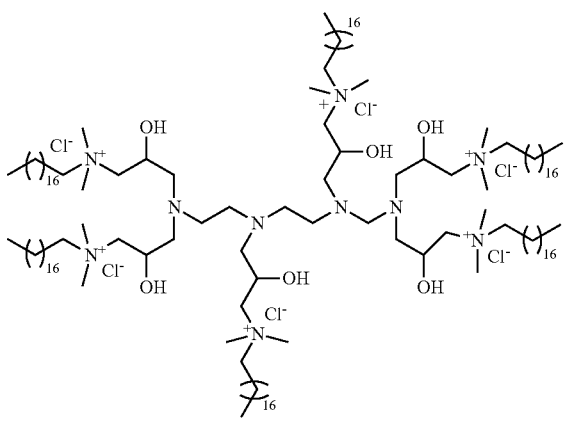
* * * * *

UNITED STATES PATENT AND TRADEMARK OFFICE
CERTIFICATE OF CORRECTION

PATENT NO. : 10,563,042 B2
APPLICATION NO. : 15/839502
DATED : February 18, 2020
INVENTOR(S) : Zhengang Zong et al.

Page 1 of 1

It is certified that error appears in the above-identified patent and that said Letters Patent is hereby corrected as shown below:

In the Claims

In Column 52, (Line 9) Claim 17, Line 3, please replace "triethylenetetraamine," with --triethylenetetramine,--

Signed and Sealed this
Thirtieth Day of June, 2020

Andrei Iancu
*Director of the United States Patent and Trademark Office*